United States Patent
Hacker et al.

(10) Patent No.: US 9,253,985 B2
(45) Date of Patent: *Feb. 9, 2016

(54) HERBICIDAL COMPOSITION FOR TOLERANT OR RESISTANT CEREAL CROPS

(75) Inventors: Erwin Hacker, Hochheim (DE); Hansjörg Dietrich, Liederbach am Taunus (DE); Hubert Menne, Mainz-Kastel (DE); Elmar Gatzweiler, Büdingen (DE); Frank Ziemer, Kriftel (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/111,535

(22) Filed: May 19, 2011

(65) Prior Publication Data

US 2011/0287932 A1 Nov. 24, 2011

(30) Foreign Application Priority Data

May 21, 2010 (EP) ..................................... 10163619

(51) Int. Cl.
| | |
|---|---|
| A01N 57/20 | (2006.01) |
| A01N 43/40 | (2006.01) |
| A01N 37/40 | (2006.01) |
| A01N 39/04 | (2006.01) |
| A01N 43/54 | (2006.01) |
| A01N 43/56 | (2006.01) |
| A01N 43/90 | (2006.01) |
| A01N 47/36 | (2006.01) |

(52) U.S. Cl.
CPC ................ A01N 57/20 (2013.01); A01N 43/40 (2013.01)

(58) Field of Classification Search
CPC ... A01N 43/40; A01N 57/20; A01N 2300/00; A01N 37/40; A01N 39/04; A01N 43/56; A01N 43/82; A01N 43/90; A01N 47/36; A01N 43/54
See application file for complete search history.

(56) References Cited

U.S. PATENT DOCUMENTS

| | | | |
|---|---|---|---|
| 4,168,963 A | 9/1979 | Rupp et al. | |
| 6,365,550 B1 * | 4/2002 | Feucht et al. | 504/128 |
| 6,723,681 B2 * | 4/2004 | Hacker et al. | 504/127 |
| 2002/0094934 A1 | 7/2002 | Hacker et al. | |
| 2003/0022792 A1 | 1/2003 | Hacker et al. | |
| 2007/0179059 A1 | 8/2007 | Epp et al. | |
| 2007/0179060 A1 | 8/2007 | Balko et al. | |
| 2008/0153704 A1 * | 6/2008 | Yamaji et al. | 504/136 |
| 2009/0062121 A1 * | 3/2009 | Satchivi et al. | 504/105 |
| 2010/0120618 A1 * | 5/2010 | Kotzian et al. | 504/139 |

FOREIGN PATENT DOCUMENTS

| | | |
|---|---|---|
| DE | 27 17 440 | 1/1977 |
| EP | 1652432 A2 * | 5/2006 |
| WO | 2007/082098 | 7/2007 |
| WO | 2007/120706 | 10/2007 |
| WO | 2009/029518 | 3/2009 |

OTHER PUBLICATIONS

International Search Report of PCT/EP2011/058108 mail dated Aug. 1, 2011 (3 pages).

* cited by examiner

*Primary Examiner* — Sean Basquill
*Assistant Examiner* — Mark V Stevens
(74) *Attorney, Agent, or Firm* — Miles and Stockbridge

(57) ABSTRACT

The invention provides herbicide combinations and the use of herbicide combinations for controlling harmful plants in cereal crops wherein the herbicide combination in question comprises
(A) a herbicide from the group of glufosinate derivatives of the formula (A1)

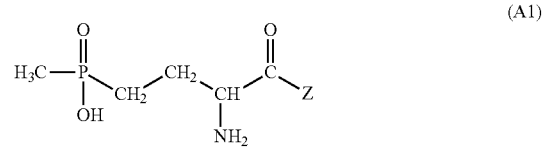

in which Z represents hydroxyl, —NHCH(CH₃)CON-HCH(CH₃)COOH or —NHCH(CH₃)CONHCH[CH₂CH(CH₃)₂]COOH,
or an ester or salt thereof, and
(B) a herbicide from the group of carboxylic acid derivatives of the formula (B1)

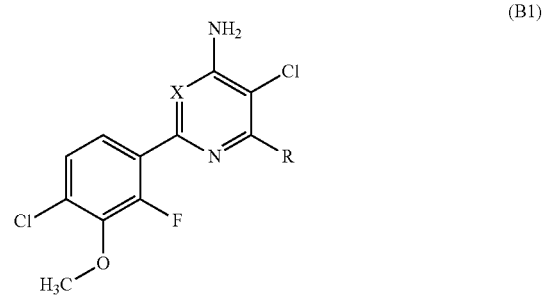

in which X represents N or CH and R represents CO₂H or a herbicidally active derivative thereof,
and the cereal crops are tolerant, if appropriate in the presence of safeners, to the herbicides (A) and (B) present in the combination.

16 Claims, No Drawings

HERBICIDAL COMPOSITION FOR TOLERANT OR RESISTANT CEREAL CROPS

CROSS REFERENCE TO RELATED APPLICATIONS

This application claims priority to European Application 10163619.9 filed May 21, 2010, the content of which is incorporated by reference in its entirety.

BACKGROUND

1. Field of the Invention

The invention relates to the field of crop protection compositions which can be used against harmful plants in tolerant or resistant crops of cereals (such as, for example, common wheat, barley, triticale, rye and oats) and comprise, as herbicidally active compounds, a combination of two or more herbicides.

2. Description of Related Art

The introduction of tolerant or resistant cereal varieties and cereal lines, in particular transgenic cereal varieties, cereal hybrids and cereal lines, adds novel active compounds which per se are not selective in conventional cereal varieties, to the conventional weed control system. The active compounds are, for example, the known broad-spectrum herbicides such as glyphosate, sulfosate, glufosinate, bilanafos (=bialaphos) and imidazolinone herbicides, which can now be employed in the tolerant crops developed specifically for them. The efficacy of these herbicides against harmful plants in the tolerant crops is high, but depends—similarly to other herbicide treatments—on the nature of the herbicide employed, its application rate, the preparation in question, the harmful plants to be controlled, the climatic conditions, the soil conditions etc. Furthermore, the herbicides exhibit weak points (zero effect) against specific species of harmful plants. Another criterion is the duration of action, or the degradation rate of the herbicide. If appropriate, changes in the sensitivity of harmful plants (development of resistance), which may occur upon prolonged use of the herbicides or within a geographical limited area, must also be taken into consideration. The loss of action against individual plants can only be compensated for to a certain extent by higher application rates of the herbicides, if at all. Moreover, there is always a demand for methods to achieve the herbicidal effect with lower application rates of active compounds. A lower application rate not only reduces the amount of an active compound required for application, but as a rule, also reduces the amount of formulation auxiliaries required. Both reduce the economic outlay and improve the eco-friendliness of the herbicide treatment.

One possibility for improving the use profile of a herbicide may consist in combining the active compound with one or more other active compounds which contribute the desired additional properties. However, the combined use of a plurality of active compounds does not infrequently lead to phenomena of a physical and biological incompatibility, for example lacking stability of a coformulation, decomposition of an active compound or antagonism in the biological action of the active compounds. In contrast, what is desired are combinations of active compounds with a favorable profile of action, high stability and, ideally, synergistically enhanced activity, which allows the application rate to be reduced in comparison with the individual application of the active compounds to be combined.

Compounds (A) and (B) are known. Compounds of type (A1) are described, for example, in DE-A 2717440. Compounds of type (B1) are described, for example, in WO 2007/082098. Mixtures of these compounds with other herbicides are described, for example, in WO 2009/029518. This publication also describes synergistic mixtures of some of the (B)-components according to the invention with the total herbicide glyphosate, but not their use in tolerant crops, but only synergism with respect to the herbicidal action against weed grasses/broad-leaved weeds.

WO 2007/120706 A2 describes synergistic herbicide combinations (01, p. 1, lines 8-11) comprising a pyrimidinecarboxylic acid of the formula I (see p. 2, lines 6-16) and a second herbicide (for example a GS (glutamine synthase) inhibitor (01, p. 2, line 25)) or herbicide safener.

US-A-2002/094934 describes herbicide combinations comprising a herbicide A (see p. 1, A. 6-14) and a herbicide B (see pp. 1-2, A. 15-19).

US-A-2007/179059 describes pyrimidinecarboxylic acids and their derivatives of the formula I (see 04, pp. 1-2).

Surprisingly, it has now been found that certain active compounds from the class of the abovementioned broad-spectrum herbicides (A) in combination with certain herbicides (B) interact in a particularly favorably (synergistic) manner when they are employed in the cereal crops which are suitable for the selective use of the first-mentioned herbicides.

SUMMARY

Accordingly, the present invention provides the use of herbicide combinations for controlling harmful plants in cereal crops (preferably in crops of wheat, oats or barley, particularly preferably in wheat crops) wherein the herbicide combination in question comprises (A) a herbicide from the group of the compounds of the formula (A1)

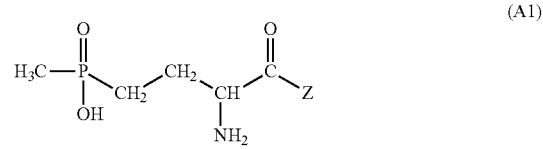

in which Z represents hydroxyl, —NHCH(CH₃)CONHCH(CH₃)COOH or —NHCH(CH₃)CONHCH[CH₂CH(CH₃)₂]COOH,
or an ester or salt thereof, and (B) a herbicide of the formula (B1)

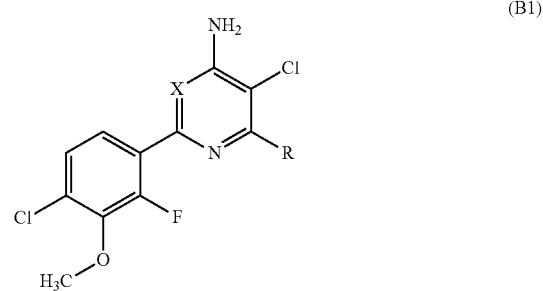

in which X represents N or CH and R represents CO₂H or a herbicidally active derivative thereof,
and the cereal crops are tolerant, if appropriate in the presence of safeners, to the herbicides (A) and (B) present in the combination.

DETAILED DESCRIPTION OF A PREFERRED EMBODIMENT

Preferred components (A) are in each case per se
glufosinate and its salts,
L-glufosinate and its salts and
bialaphos and its salts.

Particularly preferred components (A) are in each case per se
glufosinate-ammonium (A1.1),
L-glufosinate-ammonium (A1.2) and
bialaphos-sodium (A1.3).

Compounds of the formula (B1) in which the substituent R is $CO_2H$ (i.e. carboxylic acid function), are taken to be those compounds which bind to the active site of a plant enzyme or of a receptor and thereby bring about a herbicidal effect on the plant. Other compounds of the formula (B1) in which the substituent R is a group which can be converted within plants or the environment into a carboxylic acid function (i.e. $CO_2H$) produce a similar herbicidal effect and are likewise encompassed by the present invention. Consequently, within the context of the present invention, a herbicidally active derivative is understood as meaning in particular salts, esters, carboxamides, acyl hydrazides, imidates, thioimidates, amidines, acyl halides, acyl cyanides, acid anhydrides, ethers, acetals, orthoesters, carboxaldehydes, oximes, hydrazones, thio acids, thio esters, dithiolesters, nitriles and any other desired carboxylic acid derivative which does not cancel the herbicidal effect of the compound of the formula (B1) and provides the carboxylic acid function in plants and/or in the soil for example through hydrolysis, oxidation, reduction or another type of metabolism. Here, the carboxylic acid function may be present in dissociated or non-dissociated form, depending on the pH.

By addition of a suitable inorganic or organic acid, such as, for example, HCl, HBr, $H_2SO_4$ or $HNO_3$, but also oxalic acid or sulfonic acids, onto a basic group, such as, for example, amino or alkylamino, the compounds of the formula (B1) may also form salts. Suitable substituents present in deprotonated form, such as, for example, sulfonic acids or carboxylic acids, may form inner salts with groups which for their part can be protonated, such as amino groups. Salts may also be formed by replacing the hydrogen of suitable substituents, such as, for example, sulfonic acids or carboxylic acids, by an agriculturally suitable cation. These salts are, for example, metal salts, in particular alkali metal salts or alkaline earth metal salts, especially sodium salts and potassium salts, or else ammonium salts, salts with organic amines or quaternary ammonium salts having cations of the formula $[NRR'R''R''']^+$ in which R to R''', in each case independently of one another, represent an organic radical, in particular alkyl, aryl, aralkyl or alkylaryl.

The compounds of the formula (B1) may in particular also comprise N-oxides. Such pyridine N-oxides can be obtained by oxidation of the corresponding pyridines. Suitable oxidation methods are described, for example, in Houben-Weyl, Methoden der organischen Chemie [Methods of Organic Chemistry], expanded and subsequent volumes to the 4th edition, volume E 7b, p. 565 f.

Preferred components (B) are in each case per se:
4-amino-3-chloro-6-(4-chloro-2-fluoro-3-methoxyphenyl)pyridine-2-carboxylic acid (B1.0)
methyl 4-amino-3-chloro-6-(4-chloro-2-fluoro-3-methoxyphenyl)pyridine-2-carboxylate (B1.1)
ethyl 4-amino-3-chloro-6-(4-chloro-2-fluoro-3-methoxyphenyl)pyridine-2-carboxylate (B1.2)
n-propyl 4-amino-3-chloro-6-(4-chloro-2-fluoro-3-methoxyphenyl)pyridine-2-carboxylate (B1.3)
isopropyl 4-amino-3-chloro-6-(4-chloro-2-fluoro-3-methoxyphenyl)pyridine-2-carboxylate (B1.4)
n-butyl 4-amino-3-chloro-6-(4-chloro-2-fluoro-3-methoxyphenyl)pyridine-2-carboxylate B1.5)
2-butyl 4-amino-3-chloro-6-(4-chloro-2-fluoro-3-methoxyphenyl)pyridine-2-carboxylate (B1.6)
tert-butyl 4-amino-3-chloro-6-(4-chloro-2-fluoro-3-methoxyphenyl)pyridine-2-carboxylate (B1.7)
allyl 4-amino-3-chloro-6-(4-chloro-2-fluoro-3-methoxyphenyl)pyridine-2-carboxylate (B1.8)
2-butoxyethyl 4-amino-3-chloro-6-(4-chloro-2-fluoro-3-methoxyphenyl)pyridine-2-carboxylate (B1.9)
4-amino-3-chloro-6-(4-chloro-2-fluoro-3-methoxyphenyl)pyridine-2-carboxylic acid triethylammonium salt (B1.10)
4-amino-3-chloro-6-(4-chloro-2-fluoro-3-methoxyphenyl)pyridine-2-carboxylic acid potassium salt (B1.11)
6-amino-5-chloro-2-(4-chloro-2-fluoro-3-methoxyphenyl)pyrimidine-4-carboxylic acid (B1.12)
methyl 6-amino-5-chloro-2-(4-chloro-2-fluoro-3-methoxyphenyl)pyrimidine-4-carboxylate (B1.13)
ethyl 6-amino-5-chloro-2-(4-chloro-2-fluoro-3-methoxyphenyl)pyrimidine-4-carboxylate (B1.14)
n-propyl 6-amino-5-chloro-2-(4-chloro-2-fluoro-3-methoxyphenyl)pyrimidine-4-carboxylate (B1.15)
isopropyl 6-amino-5-chloro-2-(4-chloro-2-fluoro-3-methoxyphenyl)pyrimidine-4-carboxylate (B1.16)
n-butyl 6-amino-5-chloro-2-(4-chloro-2-fluoro-3-methoxyphenyl)pyrimidine-4-carboxylate (B1.17)
2-butyl 6-amino-5-chloro-2-(4-chloro-2-fluoro-3-methoxyphenyl)pyrimidine-4-carboxylate (B1.18)
tert-butyl 6-amino-5-chloro-2-(4-chloro-2-fluoro-3-methoxyphenyl)pyrimidine-4-carboxylate (B1.19)
allyl 6-amino-5-chloro-2-(4-chloro-2-fluoro-3-methoxyphenyl)pyrimidine-4-carboxylate (B1.20)
2-butoxyethyl 6-amino-5-chloro-2-(4-chloro-2-fluoro-3-methoxyphenyl)pyrimidine-4-carboxylate (B1.21)
6-amino-5-chloro-2-(4-chloro-2-fluoro-3-methoxyphenyl)pyrimidine-4-carboxylic acid triethylammonium salt (B1.22)
6-amino-5-chloro-2-(4-chloro-2-fluoro-3-methoxyphenyl)pyrimidine-4-carboxylic acid potassium salt (B1.23)

Particularly preferred components (B) are
4-amino-3-chloro-6-(4-chloro-2-fluoro-3-methoxyphenyl)pyridine-2-carboxylic acid (B1.0) and
methyl 4-amino-3-chloro-6-(4-chloro-2-fluoro-3-methoxyphenyl)pyridine-2-carboxylate (B1.1)

In another embodiment, particularly preferred components (B) are
6-amino-5-chloro-2-(4-chloro-2-fluoro-3-methoxyphenyl)pyrimidine-4-carboxylic acid (B1.12) and
methyl 6-amino-5-chloro-2-(4-chloro-2-fluoro-3-methoxyphenyl)pyrimidine-4-carboxylate (B1.13)

The herbicide combinations according to the invention may comprise further active crop protection compounds and adjuvants and auxiliaries customary in crop protection.

The synergistic effects are observed when the active compounds (A) and (B) are applied together, but can also be observed upon split application (splitting). Another possibility is to apply the herbicides or herbicide combinations in several portions (sequential application), for example after pre-emergence applications, followed by post-emergence applications or after early post-emergence applications, followed by applications at medium or late post-emergence.

Preferred is the simultaneous application of the active compounds of the combination in question, if appropriate in several portions. However, a staggered application of the individual active compounds of a combination is also possible and may be advantageous in individual cases. Other crop protection agents such as fungicides, insecticides, acaricides and the like, and/or various auxiliaries, adjuvants and/or fertilizer applications may also be integrated into this system application.

The synergistic effects allow the application rates of the individual active compounds to be reduced, a more potent action against the same species of harmful plant combined with the same application rate, the control of species to which the action has hitherto not extended (zero effect), an extended application period and/or a reduced number of required individual applications and—as a result for the user—economically and ecologically more advantageous weed control systems.

For example, the combinations of (A)+(B) according to the invention allow synergistically increased effects which far and unexpectedly exceed the effects which can be achieved with the individual active compounds (A) and (B).

The invention provides herbicide combinations which can be used particularly favorably in tolerant cereal crops.

The herbicides (A1.1) to (A1.3) mentioned are taken up via the green parts of the plants and are known as broad-band herbicides or total herbicides; they are inhibitors of the enzyme glutamine synthetase in plants; see "The Pesticide Manual" 11th Edition, British Crop Protection Council 1997, pp. 643-645 and 120-121.

The combinations according to the invention generally require an application rate of the active compound (A), for example the racemate of glufosinate, in the range of from 2.5 to 2500 g of AS/ha (=gram of active substance per hectare), preferably from 3.0 to 2000 g of AS/ha, particularly preferably 5.0-1500 g of AS/ha. Corresponding amounts, converted into mole per hectare, also apply to (A1.1), (A1.2) and (A1.3).

The combinations are expediently employed in cereal crops which are tolerant to the compounds (A1). Here, the tolerance may have been generated by breeding or mutation selection (for example analogously to the commercially available Clearfield® wheat crops from BASF, which are tolerant to the imidazolinone herbicide), or else by genetic engineering. Some genetically engineered cereal crops are already known, cf. EP-A-0 242 246, EP-A-0 242 236, EP-A-0 257 542, EP-A-0 275 957, EP-A-0 513 054).

The application rates of the herbicides (B) may vary strongly. The following ranges are expedient:
generally 0.5-500 g of AS/ha, preferably 1-400 g of AS/ha, particularly preferably: 2-300 g of AS/ha (cf. the statements for the group of compounds (A))

The ratios of the compounds (A) and (B) follow from the application rates mentioned for the individual compounds.

Of particular interest is the use of each particular combination listed below in the form of a table.

TABLE 1

| No. | Active compound (A) | Active compound (B) |
|---|---|---|
| 1 | A1.1 | B1.0 |
| 2 | A1.1 | B1.1 |
| 3 | A1.1 | B1.2 |
| 4 | A1.1 | B1.3 |
| 5 | A1.1 | B1.4 |
| 6 | A1.1 | B1.5 |
| 7 | A1.1 | B1.6 |

TABLE 1-continued

| No. | Active compound (A) | Active compound (B) |
|---|---|---|
| 8 | A1.1 | B1.7 |
| 9 | A1.1 | B1.8 |
| 10 | A1.1 | B1.9 |
| 11 | A1.1 | B1.10 |
| 12 | A1.1 | B1.11 |
| 13 | A1.1 | B1.12 |
| 14 | A1.1 | B1.13 |
| 15 | A1.1 | B1.14 |
| 16 | A1.1 | B1.15 |
| 17 | A1.1 | B1.16 |
| 18 | A1.1 | B1.17 |
| 19 | A1.1 | B1.18 |
| 20 | A1.1 | B1.19 |
| 21 | A1.1 | B1.20 |
| 22 | A1.1 | B1.21 |
| 23 | A1.1 | B1.22 |
| 24 | A1.1 | B1.23 |
| 25 | A1.2 | B1.0 |
| 26 | A1.2 | B1.1 |
| 27 | A1.2 | B1.2 |
| 28 | A1.2 | B1.3 |
| 29 | A1.2 | B1.4 |
| 30 | A1.2 | B1.5 |
| 31 | A1.2 | B1.6 |
| 32 | A1.2 | B1.7 |
| 33 | A1.2 | B1.8 |
| 34 | A1.2 | B1.9 |
| 35 | A1.2 | B1.10 |
| 36 | A1.2 | B1.11 |
| 37 | A1.2 | B1.12 |
| 38 | A1.2 | B1.13 |
| 39 | A1.2 | B1.14 |
| 40 | A1.2 | B1.15 |
| 41 | A1.2 | B1.16 |
| 42 | A1.2 | B1.17 |
| 43 | A1.2 | B1.18 |
| 44 | A1.2 | B1.19 |
| 45 | A1.2 | B1.20 |
| 46 | A1.2 | B1.21 |
| 47 | A1.2 | B1.22 |
| 48 | A1.2 | B1.23 |
| 49 | A1.3 | B1.0 |
| 50 | A1.3 | B1.1 |
| 51 | A1.3 | B1.2 |
| 52 | A1.3 | B1.3 |
| 53 | A1.3 | B1.4 |
| 54 | A1.3 | B1.5 |
| 55 | A1.3 | B1.6 |
| 56 | A1.3 | B1.7 |
| 57 | A1.3 | B1.8 |
| 58 | A1.3 | B1.9 |
| 59 | A1.3 | B1.10 |
| 60 | A1.3 | B1.11 |
| 61 | A1.3 | B1.12 |
| 62 | A1.3 | B1.13 |
| 63 | A1.3 | B1.14 |
| 64 | A1.3 | B1.15 |
| 65 | A1.3 | B1.16 |
| 66 | A1.3 | B1.17 |
| 67 | A1.3 | B1.18 |
| 68 | A1.3 | B1.19 |
| 69 | A1.3 | B1.20 |
| 70 | A1.3 | B1.21 |
| 71 | A1.3 | B1.22 |
| 72 | A1.3 | B1.23 |

In individual cases, it may be expedient to combine one or more compounds (A) with more than one compound (B).

Moreover, the combinations according to the invention can be employed together with other active compounds, for example from the group of the fungicides, insecticides and plant growth regulators, or from the group of the additives and formulation auxiliaries customary in crop protection. Additives are, for example, fertilizers, wetting agents, oils and colorants.

Combinations comprising one or more further active compounds of a different structure [active compounds (C)], for example safeners, plant growth regulators or other herbicides, are likewise in accordance with the invention. For combinations of the latter type of three or more active compounds, the preferred conditions illustrated above for the two-component combinations according to the invention primarily also apply if they comprise the two-component combinations according to the invention and with respect to the two-component combination according to the invention. If cereal crops do not have any natural tolerance for the active compound (C), such a tolerance has to be generated by mutation selection, breeding or genetical engineering to allow the uses according to the invention, or the addition of safeners becomes obligatory.

Suitable active compounds (C) are, for example, the safeners benoxacor, cloquintocet(-mexyl), cyometrinil, cyprosulfamide, dichlormid, fenchlorazole(-ethyl), fenclorim, flurazole, fluxofenim, furilazole, isoxadifen(-ethyl), mefenpyr(-diethyl), naphthalic anhydride, oxabetrinil, "AD-67" or "MON 4660" (=3-dichloroacetyl-1-oxa-3-aza-spiro[4,5]decane), "TI-35" (=1-dichloroacetylazepane), "dimepiperate" or "MY-93" (=S-1-methyl-1-phenylethyl piperidine-1-thiocarboxylate), "daimuron" or "SK 23" (=1-(1-methyl-1-phenylethyl)-3-p-tolylurea) or "cumyluron"="JC-940" (=3-(2-chlorophenylmethyl)-1-(1-methyl-1-phenylethyl)urea) or the herbicides and plant growth regulators below:
acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryn, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glyphosate, glyphosate-diammonium, glyphosate-isopropylammonium, glyphosate-potassium, H-9201, i.e. O-(2,4-dimethyl-6-nitrophenyl) O-ethyl isopropylphosphoroamidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorphenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesosulfuron-methyl-sodium, mesotrione, methabenzthiazuron, metam, metamifop, metamitron, metazachlor, metazasulfuron, methazole, methiopyrsulfuron, methiozolin, methoxyphenone, methyldymron, 1-methylcyclopropen, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron-ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribarnbenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl-5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and also the following compounds:

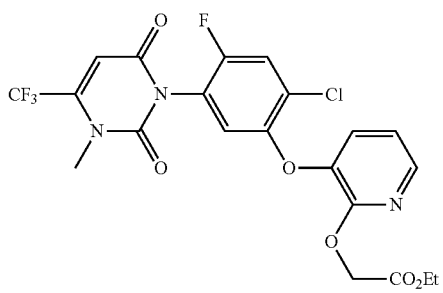

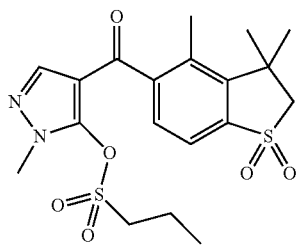

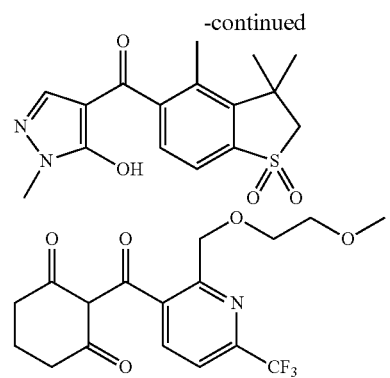

In a preferred embodiment, the compositions which can be used according to the invention comprise, as active compound (C), cloquintocet(-mexyl) (C1), cyprosulfamide (C2), isoxadifen(-ethyl) (C3) or mefenpyr(-diethyl) (C4).

In another preferred embodiment, the compositions which can be used according to the invention comprise, as active compound (C), amidosulfuron (C5), bentazone (C6), bromoxynil (C7), carfentrazone (C8), carfentrazone-ethyl (C9), chlorsulfuron (C10), cinidon-ethyl (C11), clodinafop-propargyl (C12), 2,4-D (C13), dicamba (C14), diclofop (C15), diclofop-methyl (C16), diclofop-P-methyl (C17), diflufenican (C18), ethephon (C19), ethoxysulfuron (C20), fenoxaprop (C21), fenoxaprop-P(C22), fenoxaprop-ethyl (C23), fenoxaprop-P-ethyl (C24), florasulam (C25), flucarbazone (C26), flucarbazone-sodium (C27), flufenacet (thiafluamide) (C28), fluoroglycofen (C29), fluoroxypyr (C30), fluoroxypyr-meptyl (C31), flurtamone (C32), glyphosate (C33), glyphosate-isopropylammonium (C34), glyphosate-diammonium (C35), glyphosate-potassium (C36), imazamox (C37), imazamox-ammonium (C38), iodosulfuron (C39), iodosulfuron-methyl-sodium (C40), ioxynil (C41), isoproturon (C42), MCPA (C43), mecoprop (C44), mecoprop-sodium (C45), mecoprop-butotyl (C46), mecoprop-P-butotyl (C47), mecoprop-P-dimethylammonium (C48), mecoprop-P-2-ethylhexyl (C49), mecoprop-P-potassium (C50), mesosulfuron (C51), mesosulfuron-methyl-sodium (C52), metribuzin (C53), metsulfuron (C54), metsulfuron-methyl (C55), pendimethalin (C56), penoxsulam (C57), pinoxaden (C58), propoxycarbazone (C59), propoxycarbazone-sodium (C60), pyrasulfutole (C61), pyroxsulam (C62), saflufenacil (C63), sulfosulfuron (C64), thiencarbazone (C65), thiencarbazone-methyl (C66), thifensulfuron (C67), thifensulfuron-methyl (C68), tralkoxydim (C69), triasulfuron (C70), tribenuron (C71), tribenuron-methyl (C72) or tritosulfuron (C73).

In a particularly preferred embodiment, the compositions which can be used according to the invention comprise, as active compound (C), amidosulfuron (C5), bromoxynil (C7), diclofop (C15), diflufenican (C18), fenoxaprop (C21), fenoxaprop-P (C22), fenoxaprop-ethyl (C23), fenoxaprop-P-ethyl (C24), flufenacet (thiafluamide) (C28), flurtamone (C32), iodosulfuron-methyl-sodium (C40), ioxynil (C41), isoproturon (C42), mesosulfuron (C51), mesosulfuron-methyl (C52), propoxycarbazone (C59), propoxycarbazone-sodium (C60), pyrasulfutole (C61) or thiencarbazone (C65).

Suitable in accordance with the invention, in a manner which should be emphasized, are thus also in each case per se the three-component combinations, listed below in the form of a table, of active compounds:

TABLE 2

| Active compound (A) | Active compound (B) | Active compound (C) |
|---|---|---|
| A1.1 | B1.0 | (C1) |
| A1.1 | B1.0 | (C2) |
| A1.1 | B1.0 | (C3) |
| A1.1 | B1.0 | (C4) |
| A1.1 | B1.0 | (C5) |
| A1.1 | B1.0 | (C7) |
| A1.1 | B1.0 | (C9) |
| A1.1 | B1.0 | (C15) |
| A1.1 | B1.0 | (C18) |
| A1.1 | B1.0 | (C21) |
| A1.1 | B1.0 | (C22) |
| A1.1 | B1.0 | (C23) |
| A1.1 | B1.0 | (C24) |
| A1.1 | B1.0 | (C25) |
| A1.1 | B1.0 | (C28) |
| A1.1 | B1.0 | (C32) |
| A1.1 | B1.0 | (C37) |
| A1.1 | B1.0 | (C40) |
| A1.1 | B1.0 | (C41) |
| A1.1 | B1.0 | (C42) |
| A1.1 | B1.0 | (C43) |
| A1.1 | B1.0 | (C51) |
| A1.1 | B1.0 | (C52) |
| A1.1 | B1.0 | (C57) |
| A1.1 | B1.0 | (C58) |
| A1.1 | B1.0 | (C59) |
| A1.1 | B1.0 | (C60) |
| A1.1 | B1.0 | (C61) |
| A1.1 | B1.0 | (C62) |
| A1.1 | B1.0 | (C65) |
| A1.1 | B1.0 | (C66) |
| A1.1 | B1.0 | (C71) |
| A1.1 | B1.0 | (C74) |
| A1.1 | B1.1 | (C1) |
| A1.1 | B1.1 | (C2) |
| A1.1 | B1.1 | (C3) |
| A1.1 | B1.1 | (C4) |
| A1.1 | B1.1 | (C5) |
| A1.1 | B1.1 | (C7) |
| A1.1 | B1.1 | (C9) |
| A1.1 | B1.1 | (C15) |
| A1.1 | B1.1 | (C18) |
| A1.1 | B1.1 | (C21) |
| A1.1 | B1.1 | (C22) |
| A1.1 | B1.1 | (C23) |
| A1.1 | B1.1 | (C25) |
| A1.1 | B1.1 | (C24) |
| A1.1 | B1.1 | (C28) |
| A1.1 | B1.1 | (C32) |
| A1.1 | B1.1 | (C37) |
| A1.1 | B1.1 | (C40) |
| A1.1 | B1.1 | (C41) |
| A1.1 | B1.1 | (C42) |
| A1.1 | B1.1 | (C43) |
| A1.1 | B1.1 | (C51) |
| A1.1 | B1.1 | (C52) |
| A1.1 | B1.1 | (C57) |
| A1.1 | B1.1 | (C58) |
| A1.1 | B1.1 | (C59) |
| A1.1 | B1.1 | (C60) |
| A1.1 | B1.1 | (C61) |
| A1.1 | B1.1 | (C62) |
| A1.1 | B1.1 | (C65) |
| A1.1 | B1.1 | (C66) |
| A1.1 | B1.1 | (C71) |
| A1.1 | B1.1 | (C74) |
| A1.1 | B1.2 | (C1) |
| A1.1 | B1.2 | (C2) |
| A1.1 | B1.2 | (C3) |
| A1.1 | B1.2 | (C4) |
| A1.1 | B1.2 | (C5) |
| A1.1 | B1.2 | (C7) |
| A1.1 | B1.2 | (C9) |
| A1.1 | B1.2 | (C12) |
| A1.1 | B1.2 | (C13) |
| A1.1 | B1.2 | (C15) |
| A1.1 | B1.2 | (C18) |
| A1.1 | B1.2 | (C21) |
| A1.1 | B1.2 | (C22) |
| A1.1 | B1.2 | (C23) |
| A1.1 | B1.2 | (C24) |
| A1.1 | B1.2 | (C25) |
| A1.1 | B1.2 | (C28) |
| A1.1 | B1.2 | (C32) |
| A1.1 | B1.2 | (C37) |
| A1.1 | B1.2 | (C40) |
| A1.1 | B1.2 | (C41) |
| A1.1 | B1.2 | (C42) |
| A1.1 | B1.2 | (C43) |
| A1.1 | B1.2 | (C51) |
| A1.1 | B1.2 | (C52) |
| A1.1 | B1.2 | (C57) |
| A1.1 | B1.2 | (C58) |
| A1.1 | B1.2 | (C59) |
| A1.1 | B1.2 | (C60) |
| A1.1 | B1.2 | (C61) |
| A1.1 | B1.2 | (C62) |
| A1.1 | B1.2 | (C65) |
| A1.1 | B1.2 | (C66) |
| A1.1 | B1.2 | (C71) |
| A1.1 | B1.2 | (C74) |
| A1.1 | B1.3 | (C1) |
| A1.1 | B1.3 | (C2) |
| A1.1 | B1.3 | (C3) |
| A1.1 | B1.3 | (C4) |
| A1.1 | B1.3 | (C5) |
| A1.1 | B1.3 | (C7) |
| A1.1 | B1.3 | (C9) |
| A1.1 | B1.3 | (C12) |
| A1.1 | B1.3 | (C13) |
| A1.1 | B1.3 | (C15) |
| A1.1 | B1.3 | (C18) |
| A1.1 | B1.3 | (C21) |
| A1.1 | B1.3 | (C22) |
| A1.1 | B1.3 | (C23) |
| A1.1 | B1.3 | (C24) |
| A1.1 | B1.3 | (C25) |
| A1.1 | B1.3 | (C28) |
| A1.1 | B1.3 | (C32) |
| A1.1 | B1.3 | (C37) |
| A1.1 | B1.3 | (C40) |
| A1.1 | B1.3 | (C41) |
| A1.1 | B1.3 | (C42) |
| A1.1 | B1.3 | (C43) |
| A1.1 | B1.3 | (C51) |
| A1.1 | B1.3 | (C52) |
| A1.1 | B1.3 | (C57) |
| A1.1 | B1.3 | (C58) |
| A1.1 | B1.3 | (C59) |
| A1.1 | B1.3 | (C60) |
| A1.1 | B1.3 | (C61) |
| A1.1 | B1.3 | (C62) |
| A1.1 | B1.3 | (C65) |
| A1.1 | B1.3 | (C66) |
| A1.1 | B1.3 | (C71) |
| A1.1 | B1.3 | (C74) |
| A1.1 | B1.4 | (C1) |
| A1.1 | B1.4 | (C2) |
| A1.1 | B1.4 | (C3) |
| A1.1 | B1.4 | (C4) |
| A1.1 | B1.4 | (C5) |
| A1.1 | B1.4 | (C7) |
| A1.1 | B1.4 | (C9) |
| A1.1 | B1.4 | (C12) |
| A1.1 | B1.4 | (C13) |
| A1.1 | B1.4 | (C15) |
| A1.1 | B1.4 | (C18) |
| A1.1 | B1.4 | (C21) |
| A1.1 | B1.4 | (C22) |
| A1.1 | B1.4 | (C23) |
| A1.1 | B1.4 | (C24) |
| A1.1 | B1.4 | (C25) |

TABLE 2-continued

| Active compound (A) | Active compound (B) | Active compound (C) |
|---|---|---|
| A1.1 | B1.4 | (C28) |
| A1.1 | B1.4 | (C32) |
| A1.1 | B1.4 | (C37) |
| A1.1 | B1.4 | (C40) |
| A1.1 | B1.4 | (C41) |
| A1.1 | B1.4 | (C42) |
| A1.1 | B1.4 | (C43) |
| A1.1 | B1.4 | (C51) |
| A1.1 | B1.4 | (C52) |
| A1.1 | B1.4 | (C57) |
| A1.1 | B1.4 | (C58) |
| A1.1 | B1.4 | (C59) |
| A1.1 | B1.4 | (C60) |
| A1.1 | B1.4 | (C61) |
| A1.1 | B1.4 | (C62) |
| A1.1 | B1.4 | (C65) |
| A1.1 | B1.4 | (C66) |
| A1.1 | B1.4 | (C71) |
| A1.1 | B1.4 | (C74) |
| A1.1 | B1.5 | (C1) |
| A1.1 | B1.5 | (C2) |
| A1.1 | B1.5 | (C3) |
| A1.1 | B1.5 | (C4) |
| A1.1 | B1.5 | (C5) |
| A1.1 | B1.5 | (C7) |
| A1.1 | B1.5 | (C9) |
| A1.1 | B1.5 | (C12) |
| A1.1 | B1.5 | (C13) |
| A1.1 | B1.5 | (C15) |
| A1.1 | B1.5 | (C18) |
| A1.1 | B1.5 | (C21) |
| A1.1 | B1.5 | (C22) |
| A1.1 | B1.5 | (C23) |
| A1.1 | B1.5 | (C24) |
| A1.1 | B1.5 | (C25) |
| A1.1 | B1.5 | (C28) |
| A1.1 | B1.5 | (C32) |
| A1.1 | B1.5 | (C37) |
| A1.1 | B1.5 | (C40) |
| A1.1 | B1.5 | (C41) |
| A1.1 | B1.5 | (C42) |
| A1.1 | B1.5 | (C43) |
| A1.1 | B1.5 | (C51) |
| A1.1 | B1.5 | (C52) |
| A1.1 | B1.5 | (C57) |
| A1.1 | B1.5 | (C58) |
| A1.1 | B1.5 | (C59) |
| A1.1 | B1.5 | (C60) |
| A1.1 | B1.5 | (C61) |
| A1.1 | B1.5 | (C62) |
| A1.1 | B1.5 | (C65) |
| A1.1 | B1.5 | (C66) |
| A1.1 | B1.5 | (C71) |
| A1.1 | B1.5 | (C74) |
| A1.1 | B1.6 | (C1) |
| A1.1 | B1.6 | (C2) |
| A1.1 | B1.6 | (C3) |
| A1.1 | B1.6 | (C4) |
| A1.1 | B1.6 | (C5) |
| A1.1 | B1.6 | (C7) |
| A1.1 | B1.6 | (C9) |
| A1.1 | B1.6 | (C12) |
| A1.1 | B1.6 | (C13) |
| A1.1 | B1.6 | (C15) |
| A1.1 | B1.6 | (C18) |
| A1.1 | B1.6 | (C21) |
| A1.1 | B1.6 | (C22) |
| A1.1 | B1.6 | (C23) |
| A1.1 | B1.6 | (C24) |
| A1.1 | B1.6 | (C25) |
| A1.1 | B1.6 | (C28) |
| A1.1 | B1.6 | (C32) |
| A1.1 | B1.6 | (C37) |
| A1.1 | B1.6 | (C40) |
| A1.1 | B1.6 | (C41) |
| A1.1 | B1.6 | (C42) |
| A1.1 | B1.6 | (C43) |
| A1.1 | B1.6 | (C51) |
| A1.1 | B1.6 | (C52) |
| A1.1 | B1.6 | (C57) |
| A1.1 | B1.6 | (C58) |
| A1.1 | B1.6 | (C59) |
| A1.1 | B1.6 | (C60) |
| A1.1 | B1.6 | (C61) |
| A1.1 | B1.6 | (C62) |
| A1.1 | B1.6 | (C65) |
| A1.1 | B1.6 | (C66) |
| A1.1 | B1.6 | (C71) |
| A1.1 | B1.6 | (C74) |
| A1.1 | B1.7 | (C1) |
| A1.1 | B1.7 | (C2) |
| A1.1 | B1.7 | (C3) |
| A1.1 | B1.7 | (C4) |
| A1.1 | B1.7 | (C5) |
| A1.1 | B1.7 | (C7) |
| A1.1 | B1.7 | (C9) |
| A1.1 | B1.7 | (C12) |
| A1.1 | B1.7 | (C13) |
| A1.1 | B1.7 | (C15) |
| A1.1 | B1.7 | (C18) |
| A1.1 | B1.7 | (C21) |
| A1.1 | B1.7 | (C22) |
| A1.1 | B1.7 | (C23) |
| A1.1 | B1.7 | (C24) |
| A1.1 | B1.7 | (C25) |
| A1.1 | B1.7 | (C28) |
| A1.1 | B1.7 | (C32) |
| A1.1 | B1.7 | (C37) |
| A1.1 | B1.7 | (C40) |
| A1.1 | B1.7 | (C41) |
| A1.1 | B1.7 | (C42) |
| A1.1 | B1.7 | (C43) |
| A1.1 | B1.7 | (C51) |
| A1.1 | B1.7 | (C52) |
| A1.1 | B1.7 | (C57) |
| A1.1 | B1.7 | (C58) |
| A1.1 | B1.7 | (C59) |
| A1.1 | B1.7 | (C60) |
| A1.1 | B1.7 | (C61) |
| A1.1 | B1.7 | (C62) |
| A1.1 | B1.7 | (C65) |
| A1.1 | B1.7 | (C66) |
| A1.1 | B1.7 | (C71) |
| A1.1 | B1.7 | (C74) |
| A1.1 | B1.8 | (C1) |
| A1.1 | B1.8 | (C2) |
| A1.1 | B1.8 | (C3) |
| A1.1 | B1.8 | (C4) |
| A1.1 | B1.8 | (C5) |
| A1.1 | B1.8 | (C7) |
| A1.1 | B1.8 | (C9) |
| A1.1 | B1.8 | (C12) |
| A1.1 | B1.8 | (C13) |
| A1.1 | B1.8 | (C15) |
| A1.1 | B1.8 | (C18) |
| A1.1 | B1.8 | (C21) |
| A1.1 | B1.8 | (C22) |
| A1.1 | B1.8 | (C23) |
| A1.1 | B1.8 | (C24) |
| A1.1 | B1.8 | (C25) |
| A1.1 | B1.8 | (C28) |
| A1.1 | B1.8 | (C32) |
| A1.1 | B1.8 | (C37) |
| A1.1 | B1.8 | (C40) |
| A1.1 | B1.8 | (C41) |
| A1.1 | B1.8 | (C42) |
| A1.1 | B1.8 | (C43) |
| A1.1 | B1.8 | (C51) |
| A1.1 | B1.8 | (C52) |
| A1.1 | B1.8 | (C57) |
| A1.1 | B1.8 | (C58) |
| A1.1 | B1.8 | (C59) |

TABLE 2-continued

| Active compound (A) | Active compound (B) | Active compound (C) |
|---|---|---|
| A1.1 | B1.8 | (C60) |
| A1.1 | B1.8 | (C61) |
| A1.1 | B1.8 | (C62) |
| A1.1 | B1.8 | (C65) |
| A1.1 | B1.8 | (C66) |
| A1.1 | B1.8 | (C71) |
| A1.1 | B1.8 | (C74) |
| A1.1 | B1.9 | (C1) |
| A1.1 | B1.9 | (C2) |
| A1.1 | B1.9 | (C3) |
| A1.1 | B1.9 | (C4) |
| A1.1 | B1.9 | (C5) |
| A1.1 | B1.9 | (C7) |
| A1.1 | B1.9 | (C9) |
| A1.1 | B1.9 | (C12) |
| A1.1 | B1.9 | (C13) |
| A1.1 | B1.9 | (C15) |
| A1.1 | B1.9 | (C18) |
| A1.1 | B1.9 | (C21) |
| A1.1 | B1.9 | (C22) |
| A1.1 | B1.9 | (C23) |
| A1.1 | B1.9 | (C24) |
| A1.1 | B1.9 | (C25) |
| A1.1 | B1.9 | (C28) |
| A1.1 | B1.9 | (C32) |
| A1.1 | B1.9 | (C37) |
| A1.1 | B1.9 | (C40) |
| A1.1 | B1.9 | (C41) |
| A1.1 | B1.9 | (C42) |
| A1.1 | B1.9 | (C43) |
| A1.1 | B1.9 | (C51) |
| A1.1 | B1.9 | (C52) |
| A1.1 | B1.9 | (C57) |
| A1.1 | B1.9 | (C58) |
| A1.1 | B1.9 | (C59) |
| A1.1 | B1.9 | (C60) |
| A1.1 | B1.9 | (C61) |
| A1.1 | B1.9 | (C62) |
| A1.1 | B1.9 | (C65) |
| A1.1 | B1.9 | (C66) |
| A1.1 | B1.9 | (C71) |
| A1.1 | B1.9 | (C74) |
| A1.1 | B1.10 | (C1) |
| A1.1 | B1.10 | (C2) |
| A1.1 | B1.10 | (C3) |
| A1.1 | B1.10 | (C4) |
| A1.1 | B1.10 | (C5) |
| A1.1 | B1.10 | (C7) |
| A1.1 | B1.10 | (C9) |
| A1.1 | B1.10 | (C12) |
| A1.1 | B1.10 | (C13) |
| A1.1 | B1.10 | (C15) |
| A1.1 | B1.10 | (C18) |
| A1.1 | B1.10 | (C21) |
| A1.1 | B1.10 | (C22) |
| A1.1 | B1.10 | (C23) |
| A1.1 | B1.10 | (C24) |
| A1.1 | B1.10 | (C25) |
| A1.1 | B1.10 | (C28) |
| A1.1 | B1.10 | (C32) |
| A1.1 | B1.10 | (C37) |
| A1.1 | B1.10 | (C40) |
| A1.1 | B1.10 | (C41) |
| A1.1 | B1.10 | (C42) |
| A1.1 | B1.10 | (C43) |
| A1.1 | B1.10 | (C51) |
| A1.1 | B1.10 | (C52) |
| A1.1 | B1.10 | (C57) |
| A1.1 | B1.10 | (C58) |
| A1.1 | B1.10 | (C59) |
| A1.1 | B1.10 | (C60) |
| A1.1 | B1.10 | (C61) |
| A1.1 | B1.10 | (C62) |
| A1.1 | B1.10 | (C65) |
| A1.1 | B1.10 | (C66) |
| A1.1 | B1.10 | (C71) |
| A1.1 | B1.10 | (C74) |
| A1.1 | B1.11 | (C1) |
| A1.1 | B1.11 | (C2) |
| A1.1 | B1.11 | (C3) |
| A1.1 | B1.11 | (C4) |
| A1.1 | B1.11 | (C5) |
| A1.1 | B1.11 | (C7) |
| A1.1 | B1.11 | (C9) |
| A1.1 | B1.11 | (C12) |
| A1.1 | B1.11 | (C13) |
| A1.1 | B1.11 | (C15) |
| A1.1 | B1.11 | (C18) |
| A1.1 | B1.11 | (C21) |
| A1.1 | B1.11 | (C22) |
| A1.1 | B1.11 | (C23) |
| A1.1 | B1.11 | (C24) |
| A1.1 | B1.11 | (C25) |
| A1.1 | B1.11 | (C28) |
| A1.1 | B1.11 | (C32) |
| A1.1 | B1.11 | (C37) |
| A1.1 | B1.11 | (C40) |
| A1.1 | B1.11 | (C41) |
| A1.1 | B1.11 | (C42) |
| A1.1 | B1.11 | (C43) |
| A1.1 | B1.11 | (C51) |
| A1.1 | B1.11 | (C52) |
| A1.1 | B1.11 | (C57) |
| A1.1 | B1.11 | (C58) |
| A1.1 | B1.11 | (C59) |
| A1.1 | B1.11 | (C60) |
| A1.1 | B1.11 | (C61) |
| A1.1 | B1.11 | (C62) |
| A1.1 | B1.11 | (C65) |
| A1.1 | B1.11 | (C66) |
| A1.1 | B1.11 | (C71) |
| A1.1 | B1.11 | (C74) |
| A1.1 | B1.12 | (C1) |
| A1.1 | B1.12 | (C2) |
| A1.1 | B1.12 | (C3) |
| A1.1 | B1.12 | (C4) |
| A1.1 | B1.12 | (C5) |
| A1.1 | B1.12 | (C7) |
| A1.1 | B1.12 | (C9) |
| A1.1 | B1.12 | (C12) |
| A1.1 | B1.12 | (C13) |
| A1.1 | B1.12 | (C15) |
| A1.1 | B1.12 | (C18) |
| A1.1 | B1.12 | (C21) |
| A1.1 | B1.12 | (C22) |
| A1.1 | B1.12 | (C23) |
| A1.1 | B1.12 | (C24) |
| A1.1 | B1.12 | (C25) |
| A1.1 | B1.12 | (C28) |
| A1.1 | B1.12 | (C32) |
| A1.1 | B1.12 | (C37) |
| A1.1 | B1.12 | (C40) |
| A1.1 | B1.12 | (C41) |
| A1.1 | B1.12 | (C42) |
| A1.1 | B1.12 | (C43) |
| A1.1 | B1.12 | (C51) |
| A1.1 | B1.12 | (C52) |
| A1.1 | B1.12 | (C57) |
| A1.1 | B1.12 | (C58) |
| A1.1 | B1.12 | (C59) |
| A1.1 | B1.12 | (C60) |
| A1.1 | B1.12 | (C61) |
| A1.1 | B1.12 | (C62) |
| A1.1 | B1.12 | (C65) |
| A1.1 | B1.12 | (C66) |
| A1.1 | B1.12 | (C71) |
| A1.1 | B1.12 | (C74) |
| A1.1 | B1.13 | (C1) |
| A1.1 | B1.13 | (C2) |
| A1.1 | B1.13 | (C3) |
| A1.1 | B1.13 | (C4) |
| A1.1 | B1.13 | (C5) |

TABLE 2-continued

| Active compound (A) | Active compound (B) | Active compound (C) |
|---|---|---|
| A1.1 | B1.13 | (C7) |
| A1.1 | B1.13 | (C9) |
| A1.1 | B1.13 | (C12) |
| A1.1 | B1.13 | (C13) |
| A1.1 | B1.13 | (C15) |
| A1.1 | B1.13 | (C18) |
| A1.1 | B1.13 | (C21) |
| A1.1 | B1.13 | (C22) |
| A1.1 | B1.13 | (C23) |
| A1.1 | B1.13 | (C24) |
| A1.1 | B1.13 | (C25) |
| A1.1 | B1.13 | (C28) |
| A1.1 | B1.13 | (C32) |
| A1.1 | B1.13 | (C37) |
| A1.1 | B1.13 | (C40) |
| A1.1 | B1.13 | (C41) |
| A1.1 | B1.13 | (C42) |
| A1.1 | B1.13 | (C43) |
| A1.1 | B1.13 | (C51) |
| A1.1 | B1.13 | (C52) |
| A1.1 | B1.13 | (C57) |
| A1.1 | B1.13 | (C58) |
| A1.1 | B1.13 | (C57) |
| A1.1 | B1.13 | (C58) |
| A1.1 | B1.13 | (C59) |
| A1.1 | B1.13 | (C60) |
| A1.1 | B1.13 | (C61) |
| A1.1 | B1.13 | (C62) |
| A1.1 | B1.13 | (C65) |
| A1.1 | B1.13 | (C66) |
| A1.1 | B1.13 | (C71) |
| A1.1 | B1.13 | (C74) |
| A1.1 | B1.14 | (C1) |
| A1.1 | B1.14 | (C2) |
| A1.1 | B1.14 | (C3) |
| A1.1 | B1.14 | (C4) |
| A1.1 | B1.14 | (C5) |
| A1.1 | B1.14 | (C7) |
| A1.1 | B1.14 | (C9) |
| A1.1 | B1.14 | (C12) |
| A1.1 | B1.14 | (C13) |
| A1.1 | B1.14 | (C15) |
| A1.1 | B1.14 | (C18) |
| A1.1 | B1.14 | (C21) |
| A1.1 | B1.14 | (C22) |
| A1.1 | B1.14 | (C23) |
| A1.1 | B1.14 | (C24) |
| A1.1 | B1.14 | (C25) |
| A1.1 | B1.14 | (C25) |
| A1.1 | B1.14 | (C28) |
| A1.1 | B1.14 | (C32) |
| A1.1 | B1.14 | (C37) |
| A1.1 | B1.14 | (C40) |
| A1.1 | B1.14 | (C41) |
| A1.1 | B1.14 | (C42) |
| A1.1 | B1.14 | (C43) |
| A1.1 | B1.14 | (C51) |
| A1.1 | B1.14 | (C52) |
| A1.1 | B1.14 | (C57) |
| A1.1 | B1.14 | (C58) |
| A1.1 | B1.14 | (C59) |
| A1.1 | B1.14 | (C60) |
| A1.1 | B1.14 | (C61) |
| A1.1 | B1.14 | (C62) |
| A1.1 | B1.14 | (C65) |
| A1.1 | B1.14 | (C66) |
| A1.1 | B1.14 | (C71) |
| A1.1 | B1.14 | (C74) |
| A1.1 | B1.15 | (C1) |
| A1.1 | B1.15 | (C2) |
| A1.1 | B1.15 | (C3) |
| A1.1 | B1.15 | (C4) |
| A1.1 | B1.15 | (C5) |
| A1.1 | B1.15 | (C7) |
| A1.1 | B1.15 | (C9) |
| A1.1 | B1.15 | (C12) |
| A1.1 | B1.15 | (C13) |
| A1.1 | B1.15 | (C15) |
| A1.1 | B1.15 | (C18) |
| A1.1 | B1.15 | (C21) |
| A1.1 | B1.15 | (C22) |
| A1.1 | B1.15 | (C23) |
| A1.1 | B1.15 | (C24) |
| A1.1 | B1.15 | (C25) |
| A1.1 | B1.15 | (C25) |
| A1.1 | B1.15 | (C28) |
| A1.1 | B1.15 | (C32) |
| A1.1 | B1.15 | (C37) |
| A1.1 | B1.15 | (C40) |
| A1.1 | B1.15 | (C41) |
| A1.1 | B1.15 | (C42) |
| A1.1 | B1.15 | (C43) |
| A1.1 | B1.15 | (C51) |
| A1.1 | B1.15 | (C52) |
| A1.1 | B1.15 | (C57) |
| A1.1 | B1.15 | (C58) |
| A1.1 | B1.15 | (C57) |
| A1.1 | B1.15 | (C58) |
| A1.1 | B1.15 | (C59) |
| A1.1 | B1.15 | (C60) |
| A1.1 | B1.15 | (C61) |
| A1.1 | B1.15 | (C62) |
| A1.1 | B1.15 | (C62) |
| A1.1 | B1.15 | (C65) |
| A1.1 | B1.15 | (C66) |
| A1.1 | B1.15 | (C71) |
| A1.1 | B1.15 | (C74) |
| A1.1 | B1.16 | (C1) |
| A1.1 | B1.16 | (C2) |
| A1.1 | B1.16 | (C3) |
| A1.1 | B1.16 | (C4) |
| A1.1 | B1.16 | (C5) |
| A1.1 | B1.16 | (C7) |
| A1.1 | B1.16 | (C9) |
| A1.1 | B1.16 | (C12) |
| A1.1 | B1.16 | (C13) |
| A1.1 | B1.16 | (C15) |
| A1.1 | B1.16 | (C18) |
| A1.1 | B1.16 | (C21) |
| A1.1 | B1.16 | (C22) |
| A1.1 | B1.16 | (C23) |
| A1.1 | B1.16 | (C24) |
| A1.1 | B1.16 | (C25) |
| A1.1 | B1.16 | (C28) |
| A1.1 | B1.16 | (C32) |
| A1.1 | B1.16 | (C37) |
| A1.1 | B1.16 | (C40) |
| A1.1 | B1.16 | (C41) |
| A1.1 | B1.16 | (C42) |
| A1.1 | B1.16 | (C43) |
| A1.1 | B1.16 | (C51) |
| A1.1 | B1.16 | (C52) |
| A1.1 | B1.16 | (C57) |
| A1.1 | B1.16 | (C58) |
| A1.1 | B1.16 | (C59) |
| A1.1 | B1.16 | (C60) |
| A1.1 | B1.16 | (C61) |
| A1.1 | B1.16 | (C62) |
| A1.1 | B1.16 | (C65) |
| A1.1 | B1.16 | (C66) |
| A1.1 | B1.16 | (C71) |
| A1.1 | B1.16 | (C74) |
| A1.1 | B1.17 | (C1) |
| A1.1 | B1.17 | (C2) |
| A1.1 | B1.17 | (C3) |
| A1.1 | B1.17 | (C4) |
| A1.1 | B1.17 | (C5) |
| A1.1 | B1.17 | (C7) |
| A1.1 | B1.17 | (C9) |
| A1.1 | B1.17 | (C12) |
| A1.1 | B1.17 | (C13) |
| A1.1 | B1.17 | (C15) |

TABLE 2-continued

| Active compound (A) | Active compound (B) | Active compound (C) |
|---|---|---|
| A1.1 | B1.17 | (C18) |
| A1.1 | B1.17 | (C21) |
| A1.1 | B1.17 | (C22) |
| A1.1 | B1.17 | (C23) |
| A1.1 | B1.17 | (C24) |
| A1.1 | B1.17 | (C25) |
| A1.1 | B1.17 | (C28) |
| A1.1 | B1.17 | (C32) |
| A1.1 | B1.17 | (C37) |
| A1.1 | B1.17 | (C40) |
| A1.1 | B1.17 | (C41) |
| A1.1 | B1.17 | (C42) |
| A1.1 | B1.17 | (C43) |
| A1.1 | B1.17 | (C51) |
| A1.1 | B1.17 | (C52) |
| A1.1 | B1.17 | (C57) |
| A1.1 | B1.17 | (C58) |
| A1.1 | B1.17 | (C59) |
| A1.1 | B1.17 | (C60) |
| A1.1 | B1.17 | (C61) |
| A1.1 | B1.17 | (C62) |
| A1.1 | B1.17 | (C65) |
| A1.1 | B1.17 | (C66) |
| A1.1 | B1.17 | (C71) |
| A1.1 | B1.17 | (C74) |
| A1.1 | B1.18 | (C1) |
| A1.1 | B1.18 | (C2) |
| A1.1 | B1.18 | (C3) |
| A1.1 | B1.18 | (C4) |
| A1.1 | B1.18 | (C5) |
| A1.1 | B1.18 | (C7) |
| A1.1 | B1.18 | (C9) |
| A1.1 | B1.18 | (C12) |
| A1.1 | B1.18 | (C13) |
| A1.1 | B1.18 | (C15) |
| A1.1 | B1.18 | (C18) |
| A1.1 | B1.18 | (C21) |
| A1.1 | B1.18 | (C22) |
| A1.1 | B1.18 | (C23) |
| A1.1 | B1.18 | (C24) |
| A1.1 | B1.18 | (C25) |
| A1.1 | B1.18 | (C28) |
| A1.1 | B1.18 | (C32) |
| A1.1 | B1.18 | (C37) |
| A1.1 | B1.18 | (C40) |
| A1.1 | B1.18 | (C41) |
| A1.1 | B1.18 | (C42) |
| A1.1 | B1.18 | (C43) |
| A1.1 | B1.18 | (C51) |
| A1.1 | B1.18 | (C52) |
| A1.1 | B1.18 | (C57) |
| A1.1 | B1.18 | (C58) |
| A1.1 | B1.18 | (C59) |
| A1.1 | B1.18 | (C60) |
| A1.1 | B1.18 | (C61) |
| A1.1 | B1.18 | (C62) |
| A1.1 | B1.18 | (C65) |
| A1.1 | B1.18 | (C66) |
| A1.1 | B1.18 | (C71) |
| A1.1 | B1.18 | (C74) |
| A1.1 | B1.19 | (C1) |
| A1.1 | B1.19 | (C2) |
| A1.1 | B1.19 | (C3) |
| A1.1 | B1.19 | (C4) |
| A1.1 | B1.19 | (C5) |
| A1.1 | B1.19 | (C7) |
| A1.1 | B1.19 | (C9) |
| A1.1 | B1.19 | (C12) |
| A1.1 | B1.19 | (C13) |
| A1.1 | B1.19 | (C15) |
| A1.1 | B1.19 | (C18) |
| A1.1 | B1.19 | (C21) |
| A1.1 | B1.19 | (C22) |
| A1.1 | B1.19 | (C23) |
| A1.1 | B1.19 | (C24) |
| A1.1 | B1.19 | (C25) |
| A1.1 | B1.19 | (C28) |
| A1.1 | B1.19 | (C32) |
| A1.1 | B1.19 | (C37) |
| A1.1 | B1.19 | (C40) |
| A1.1 | B1.19 | (C41) |
| A1.1 | B1.19 | (C42) |
| A1.1 | B1.19 | (C43) |
| A1.1 | B1.19 | (C51) |
| A1.1 | B1.19 | (C52) |
| A1.1 | B1.19 | (C57) |
| A1.1 | B1.19 | (C58) |
| A1.1 | B1.19 | (C59) |
| A1.1 | B1.19 | (C60) |
| A1.1 | B1.19 | (C61) |
| A1.1 | B1.19 | (C62) |
| A1.1 | B1.19 | (C65) |
| A1.1 | B1.19 | (C66) |
| A1.1 | B1.19 | (C71) |
| A1.1 | B1.19 | (C74) |
| A1.1 | B1.20 | (C1) |
| A1.1 | B1.20 | (C2) |
| A1.1 | B1.20 | (C3) |
| A1.1 | B1.20 | (C4) |
| A1.1 | B1.20 | (C5) |
| A1.1 | B1.20 | (C7) |
| A1.1 | B1.20 | (C9) |
| A1.1 | B1.20 | (C12) |
| A1.1 | B1.20 | (C13) |
| A1.1 | B1.20 | (C15) |
| A1.1 | B1.20 | (C18) |
| A1.1 | B1.20 | (C21) |
| A1.1 | B1.20 | (C22) |
| A1.1 | B1.20 | (C23) |
| A1.1 | B1.20 | (C24) |
| A1.1 | B1.20 | (C25) |
| A1.1 | B1.20 | (C28) |
| A1.1 | B1.20 | (C32) |
| A1.1 | B1.20 | (C37) |
| A1.1 | B1.20 | (C40) |
| A1.1 | B1.20 | (C41) |
| A1.1 | B1.20 | (C42) |
| A1.1 | B1.20 | (C43) |
| A1.1 | B1.20 | (C51) |
| A1.1 | B1.20 | (C52) |
| A1.1 | B1.20 | (C57) |
| A1.1 | B1.20 | (C58) |
| A1.1 | B1.20 | (C59) |
| A1.1 | B1.20 | (C60) |
| A1.1 | B1.20 | (C61) |
| A1.1 | B1.20 | (C62) |
| A1.1 | B1.20 | (C65) |
| A1.1 | B1.20 | (C66) |
| A1.1 | B1.20 | (C71) |
| A1.1 | B1.20 | (C74) |
| A1.1 | B1.21 | (C1) |
| A1.1 | B1.21 | (C2) |
| A1.1 | B1.21 | (C3) |
| A1.1 | B1.21 | (C4) |
| A1.1 | B1.21 | (C5) |
| A1.1 | B1.21 | (C7) |
| A1.1 | B1.21 | (C9) |
| A1.1 | B1.21 | (C12) |
| A1.1 | B1.21 | (C13) |
| A1.1 | B1.21 | (C15) |
| A1.1 | B1.21 | (C18) |
| A1.1 | B1.21 | (C21) |
| A1.1 | B1.21 | (C22) |
| A1.1 | B1.21 | (C23) |
| A1.1 | B1.21 | (C24) |
| A1.1 | B1.21 | (C25) |
| A1.1 | B1.21 | (C28) |
| A1.1 | B1.21 | (C32) |
| A1.1 | B1.21 | (C37) |
| A1.1 | B1.21 | (C40) |
| A1.1 | B1.21 | (C41) |
| A1.1 | B1.21 | (C42) |

TABLE 2-continued

| Active compound (A) | Active compound (B) | Active compound (C) |
|---|---|---|
| A1.1 | B1.21 | (C43) |
| A1.1 | B1.21 | (C51) |
| A1.1 | B1.21 | (C52) |
| A1.1 | B1.21 | (C57) |
| A1.1 | B1.21 | (C58) |
| A1.1 | B1.21 | (C59) |
| A1.1 | B1.21 | (C60) |
| A1.1 | B1.21 | (C61) |
| A1.1 | B1.21 | (C62) |
| A1.1 | B1.21 | (C65) |
| A1.1 | B1.21 | (C66) |
| A1.1 | B1.21 | (C71) |
| A1.1 | B1.21 | (C74) |
| A1.1 | B1.22 | (C1) |
| A1.1 | B1.22 | (C2) |
| A1.1 | B1.22 | (C3) |
| A1.1 | B1.22 | (C4) |
| A1.1 | B1.22 | (C5) |
| A1.1 | B1.22 | (C7) |
| A1.1 | B1.22 | (C9) |
| A1.1 | B1.22 | (C12) |
| A1.1 | B1.22 | (C13) |
| A1.1 | B1.22 | (C15) |
| A1.1 | B1.22 | (C18) |
| A1.1 | B1.22 | (C21) |
| A1.1 | B1.22 | (C22) |
| A1.1 | B1.22 | (C23) |
| A1.1 | B1.22 | (C24) |
| A1.1 | B1.22 | (C25) |
| A1.1 | B1.22 | (C28) |
| A1.1 | B1.22 | (C32) |
| A1.1 | B1.22 | (C37) |
| A1.1 | B1.22 | (C40) |
| A1.1 | B1.22 | (C41) |
| A1.1 | B1.22 | (C42) |
| A1.1 | B1.22 | (C43) |
| A1.1 | B1.22 | (C51) |
| A1.1 | B1.22 | (C52) |
| A1.1 | B1.22 | (C57) |
| A1.1 | B1.22 | (C58) |
| A1.1 | B1.22 | (C59) |
| A1.1 | B1.22 | (C60) |
| A1.1 | B1.22 | (C61) |
| A1.1 | B1.22 | (C62) |
| A1.1 | B1.22 | (C65) |
| A1.1 | B1.22 | (C66) |
| A1.1 | B1.22 | (C71) |
| A1.1 | B1.22 | (C74) |
| A1.1 | B1.23 | (C1) |
| A1.1 | B1.23 | (C2) |
| A1.1 | B1.23 | (C3) |
| A1.1 | B1.23 | (C4) |
| A1.1 | B1.23 | (C5) |
| A1.1 | B1.23 | (C7) |
| A1.1 | B1.23 | (C9) |
| A1.1 | B1.23 | (C12) |
| A1.1 | B1.23 | (C13) |
| A1.1 | B1.23 | (C15) |
| A1.1 | B1.23 | (C18) |
| A1.1 | B1.23 | (C21) |
| A1.1 | B1.23 | (C22) |
| A1.1 | B1.23 | (C23) |
| A1.1 | B1.23 | (C24) |
| A1.1 | B1.23 | (C25) |
| A1.1 | B1.23 | (C28) |
| A1.1 | B1.23 | (C32) |
| A1.1 | B1.23 | (C37) |
| A1.1 | B1.23 | (C40) |
| A1.1 | B1.23 | (C41) |
| A1.1 | B1.23 | (C42) |
| A1.1 | B1.23 | (C43) |
| A1.1 | B1.23 | (C51) |
| A1.1 | B1.23 | (C52) |
| A1.1 | B1.23 | (C57) |
| A1.1 | B1.23 | (C58) |
| A1.1 | B1.23 | (C59) |
| A1.1 | B1.23 | (C60) |
| A1.1 | B1.23 | (C61) |
| A1.1 | B1.23 | (C62) |
| A1.1 | B1.23 | (C65) |
| A1.1 | B1.23 | (C66) |
| A1.1 | B1.23 | (C71) |
| A1.1 | B1.23 | (C74) |
| A1.2 | B1.0 | (C1) |
| A1.2 | B1.0 | (C2) |
| A1.2 | B1.0 | (C3) |
| A1.2 | B1.0 | (C4) |
| A1.2 | B1.0 | (C5) |
| A1.2 | B1.0 | (C7) |
| A1.2 | B1.0 | (C9) |
| A1.2 | B1.0 | (C12) |
| A1.2 | B1.0 | (C13) |
| A1.2 | B1.0 | (C15) |
| A1.2 | B1.0 | (C18) |
| A1.2 | B1.0 | (C21) |
| A1.2 | B1.0 | (C22) |
| A1.2 | B1.0 | (C23) |
| A1.2 | B1.0 | (C24) |
| A1.2 | B1.0 | (C25) |
| A1.2 | B1.0 | (C28) |
| A1.2 | B1.0 | (C32) |
| A1.2 | B1.0 | (C37) |
| A1.2 | B1.0 | (C40) |
| A1.2 | B1.0 | (C41) |
| A1.2 | B1.0 | (C42) |
| A1.2 | B1.0 | (C43) |
| A1.2 | B1.0 | (C51) |
| A1.2 | B1.0 | (C52) |
| A1.2 | B1.0 | (C57) |
| A1.2 | B1.0 | (C58) |
| A1.2 | B1.0 | (C59) |
| A1.2 | B1.0 | (C60) |
| A1.2 | B1.0 | (C61) |
| A1.2 | B1.0 | (C62) |
| A1.2 | B1.0 | (C65) |
| A1.2 | B1.0 | (C66) |
| A1.2 | B1.0 | (C71) |
| A1.2 | B1.0 | (C74) |
| A1.2 | B1.1 | (C1) |
| A1.2 | B1.1 | (C2) |
| A1.2 | B1.1 | (C3) |
| A1.2 | B1.1 | (C4) |
| A1.2 | B1.1 | (C5) |
| A1.2 | B1.1 | (C7) |
| A1.2 | B1.1 | (C9) |
| A1.2 | B1.1 | (C12) |
| A1.2 | B1.1 | (C13) |
| A1.2 | B1.1 | (C15) |
| A1.2 | B1.1 | (C18) |
| A1.2 | B1.1 | (C21) |
| A1.2 | B1.1 | (C22) |
| A1.2 | B1.1 | (C23) |
| A1.2 | B1.1 | (C24) |
| A1.2 | B1.1 | (C25) |
| A1.2 | B1.1 | (C28) |
| A1.2 | B1.1 | (C32) |
| A1.2 | B1.1 | (C37) |
| A1.2 | B1.1 | (C40) |
| A1.2 | B1.1 | (C41) |
| A1.2 | B1.1 | (C42) |
| A1.2 | B1.1 | (C43) |
| A1.2 | B1.1 | (C51) |
| A1.2 | B1.1 | (C52) |
| A1.2 | B1.1 | (C57) |
| A1.2 | B1.1 | (C58) |
| A1.2 | B1.1 | (C59) |
| A1.2 | B1.1 | (C60) |
| A1.2 | B1.1 | (C61) |
| A1.2 | B1.1 | (C62) |
| A1.2 | B1.1 | (C65) |
| A1.2 | B1.1 | (C66) |
| A1.2 | B1.1 | (C71) |

TABLE 2-continued

| Active compound (A) | Active compound (B) | Active compound (C) |
|---|---|---|
| A1.2 | B1.1 | (C74) |
| A1.2 | B1.2 | (C1) |
| A1.2 | B1.2 | (C2) |
| A1.2 | B1.2 | (C3) |
| A1.2 | B1.2 | (C4) |
| A1.2 | B1.2 | (C5) |
| A1.2 | B1.2 | (C7) |
| A1.2 | B1.2 | (C9) |
| A1.2 | B1.2 | (C12) |
| A1.2 | B1.2 | (C13) |
| A1.2 | B1.2 | (C15) |
| A1.2 | B1.2 | (C18) |
| A1.2 | B1.2 | (C21) |
| A1.2 | B1.2 | (C22) |
| A1.2 | B1.2 | (C23) |
| A1.2 | B1.2 | (C24) |
| A1.2 | B1.2 | (C25) |
| A1.2 | B1.2 | (C28) |
| A1.2 | B1.2 | (C32) |
| A1.2 | B1.2 | (C37) |
| A1.2 | B1.2 | (C40) |
| A1.2 | B1.2 | (C41) |
| A1.2 | B1.2 | (C42) |
| A1.2 | B1.2 | (C43) |
| A1.2 | B1.2 | (C51) |
| A1.2 | B1.2 | (C52) |
| A1.2 | B1.2 | (C57) |
| A1.2 | B1.2 | (C58) |
| A1.2 | B1.2 | (C59) |
| A1.2 | B1.2 | (C60) |
| A1.2 | B1.2 | (C61) |
| A1.2 | B1.2 | (C62) |
| A1.2 | B1.2 | (C65) |
| A1.2 | B1.2 | (C66) |
| A1.2 | B1.2 | (C71) |
| A1.2 | B1.2 | (C74) |
| A1.2 | B1.3 | (C1) |
| A1.2 | B1.3 | (C2) |
| A1.2 | B1.3 | (C3) |
| A1.2 | B1.3 | (C4) |
| A1.2 | B1.3 | (C5) |
| A1.2 | B1.3 | (C7) |
| A1.2 | B1.3 | (C9) |
| A1.2 | B1.3 | (C12) |
| A1.2 | B1.3 | (C13) |
| A1.2 | B1.3 | (C15) |
| A1.2 | B1.3 | (C18) |
| A1.2 | B1.3 | (C21) |
| A1.2 | B1.3 | (C22) |
| A1.2 | B1.3 | (C23) |
| A1.2 | B1.3 | (C24) |
| A1.2 | B1.3 | (C25) |
| A1.2 | B1.3 | (C28) |
| A1.2 | B1.3 | (C32) |
| A1.2 | B1.3 | (C37) |
| A1.2 | B1.3 | (C40) |
| A1.2 | B1.3 | (C41) |
| A1.2 | B1.3 | (C42) |
| A1.2 | B1.3 | (C43) |
| A1.2 | B1.3 | (C51) |
| A1.2 | B1.3 | (C52) |
| A1.2 | B1.3 | (C57) |
| A1.2 | B1.3 | (C58) |
| A1.2 | B1.3 | (C59) |
| A1.2 | B1.3 | (C60) |
| A1.2 | B1.3 | (C61) |
| A1.2 | B1.3 | (C62) |
| A1.2 | B1.3 | (C65) |
| A1.2 | B1.3 | (C66) |
| A1.2 | B1.3 | (C71) |
| A1.2 | B1.3 | (C74) |
| A1.2 | B1.4 | (C1) |
| A1.2 | B1.4 | (C2) |
| A1.2 | B1.4 | (C3) |
| A1.2 | B1.4 | (C4) |
| A1.2 | B1.4 | (C5) |
| A1.2 | B1.4 | (C7) |
| A1.2 | B1.4 | (C9) |
| A1.2 | B1.4 | (C12) |
| A1.2 | B1.4 | (C13) |
| A1.2 | B1.4 | (C15) |
| A1.2 | B1.4 | (C18) |
| A1.2 | B1.4 | (C21) |
| A1.2 | B1.4 | (C22) |
| A1.2 | B1.4 | (C23) |
| A1.2 | B1.4 | (C24) |
| A1.2 | B1.4 | (C25) |
| A1.2 | B1.4 | (C28) |
| A1.2 | B1.4 | (C32) |
| A1.2 | B1.4 | (C37) |
| A1.2 | B1.4 | (C40) |
| A1.2 | B1.4 | (C41) |
| A1.2 | B1.4 | (C42) |
| A1.2 | B1.4 | (C43) |
| A1.2 | B1.4 | (C51) |
| A1.2 | B1.4 | (C52) |
| A1.2 | B1.4 | (C57) |
| A1.2 | B1.4 | (C58) |
| A1.2 | B1.4 | (C57) |
| A1.2 | B1.4 | (C58) |
| A1.2 | B1.4 | (C59) |
| A1.2 | B1.4 | (C60) |
| A1.2 | B1.4 | (C61) |
| A1.2 | B1.4 | (C62) |
| A1.2 | B1.4 | (C65) |
| A1.2 | B1.4 | (C66) |
| A1.2 | B1.4 | (C71) |
| A1.2 | B1.4 | (C74) |
| A1.2 | B1.5 | (C1) |
| A1.2 | B1.5 | (C2) |
| A1.2 | B1.5 | (C3) |
| A1.2 | B1.5 | (C4) |
| A1.2 | B1.5 | (C5) |
| A1.2 | B1.5 | (C7) |
| A1.2 | B1.5 | (C9) |
| A1.2 | B1.5 | (C12) |
| A1.2 | B1.5 | (C13) |
| A1.2 | B1.5 | (C15) |
| A1.2 | B1.5 | (C18) |
| A1.2 | B1.5 | (C21) |
| A1.2 | B1.5 | (C22) |
| A1.2 | B1.5 | (C23) |
| A1.2 | B1.5 | (C24) |
| A1.2 | B1.5 | (C25) |
| A1.2 | B1.5 | (C28) |
| A1.2 | B1.5 | (C32) |
| A1.2 | B1.5 | (C37) |
| A1.2 | B1.5 | (C40) |
| A1.2 | B1.5 | (C41) |
| A1.2 | B1.5 | (C42) |
| A1.2 | B1.5 | (C43) |
| A1.2 | B1.5 | (C51) |
| A1.2 | B1.5 | (C52) |
| A1.2 | B1.5 | (C57) |
| A1.2 | B1.5 | (C58) |
| A1.2 | B1.5 | (C59) |
| A1.2 | B1.5 | (C60) |
| A1.2 | B1.5 | (C61) |
| A1.2 | B1.5 | (C62) |
| A1.2 | B1.5 | (C65) |
| A1.2 | B1.5 | (C66) |
| A1.2 | B1.5 | (C71) |
| A1.2 | B1.5 | (C74) |
| A1.2 | B1.6 | (C1) |
| A1.2 | B1.6 | (C2) |
| A1.2 | B1.6 | (C3) |
| A1.2 | B1.6 | (C4) |
| A1.2 | B1.6 | (C5) |
| A1.2 | B1.6 | (C7) |
| A1.2 | B1.6 | (C9) |
| A1.2 | B1.6 | (C12) |
| A1.2 | B1.6 | (C13) |

TABLE 2-continued

| Active compound (A) | Active compound (B) | Active compound (C) |
|---|---|---|
| A1.2 | B1.6 | (C15) |
| A1.2 | B1.6 | (C18) |
| A1.2 | B1.6 | (C21) |
| A1.2 | B1.6 | (C22) |
| A1.2 | B1.6 | (C23) |
| A1.2 | B1.6 | (C24) |
| A1.2 | B1.6 | (C25) |
| A1.2 | B1.6 | (C28) |
| A1.2 | B1.6 | (C32) |
| A1.2 | B1.6 | (C37) |
| A1.2 | B1.6 | (C40) |
| A1.2 | B1.6 | (C41) |
| A1.2 | B1.6 | (C42) |
| A1.2 | B1.6 | (C43) |
| A1.2 | B1.6 | (C51) |
| A1.2 | B1.6 | (C52) |
| A1.2 | B1.6 | (C57) |
| A1.2 | B1.6 | (C58) |
| A1.2 | B1.6 | (C59) |
| A1.2 | B1.6 | (C60) |
| A1.2 | B1.6 | (C61) |
| A1.2 | B1.6 | (C62) |
| A1.2 | B1.6 | (C65) |
| A1.2 | B1.6 | (C66) |
| A1.2 | B1.6 | (C71) |
| A1.2 | B1.6 | (C74) |
| A1.2 | B1.7 | (C1) |
| A1.2 | B1.7 | (C2) |
| A1.2 | B1.7 | (C3) |
| A1.2 | B1.7 | (C4) |
| A1.2 | B1.7 | (C5) |
| A1.2 | B1.7 | (C7) |
| A1.2 | B1.7 | (C9) |
| A1.2 | B1.7 | (C12) |
| A1.2 | B1.7 | (C13) |
| A1.2 | B1.7 | (C15) |
| A1.2 | B1.7 | (C18) |
| A1.2 | B1.7 | (C21) |
| A1.2 | B1.7 | (C22) |
| A1.2 | B1.7 | (C23) |
| A1.2 | B1.7 | (C24) |
| A1.2 | B1.7 | (C25) |
| A1.2 | B1.7 | (C28) |
| A1.2 | B1.7 | (C32) |
| A1.2 | B1.7 | (C37) |
| A1.2 | B1.7 | (C40) |
| A1.2 | B1.7 | (C41) |
| A1.2 | B1.7 | (C42) |
| A1.2 | B1.7 | (C43) |
| A1.2 | B1.7 | (C51) |
| A1.2 | B1.7 | (C52) |
| A1.2 | B1.7 | (C57) |
| A1.2 | B1.7 | (C58) |
| A1.2 | B1.7 | (C59) |
| A1.2 | B1.7 | (C60) |
| A1.2 | B1.7 | (C61) |
| A1.2 | B1.7 | (C62) |
| A1.2 | B1.7 | (C65) |
| A1.2 | B1.7 | (C66) |
| A1.2 | B1.7 | (C71) |
| A1.2 | B1.7 | (C74) |
| A1.2 | B1.8 | (C1) |
| A1.2 | B1.8 | (C2) |
| A1.2 | B1.8 | (C3) |
| A1.2 | B1.8 | (C4) |
| A1.2 | B1.8 | (C5) |
| A1.2 | B1.8 | (C7) |
| A1.2 | B1.8 | (C9) |
| A1.2 | B1.8 | (C12) |
| A1.2 | B1.8 | (C13) |
| A1.2 | B1.8 | (C15) |
| A1.2 | B1.8 | (C18) |
| A1.2 | B1.8 | (C21) |
| A1.2 | B1.8 | (C22) |
| A1.2 | B1.8 | (C23) |
| A1.2 | B1.8 | (C24) |
| A1.2 | B1.8 | (C25) |
| A1.2 | B1.8 | (C28) |
| A1.2 | B1.8 | (C32) |
| A1.2 | B1.8 | (C37) |
| A1.2 | B1.8 | (C40) |
| A1.2 | B1.8 | (C41) |
| A1.2 | B1.8 | (C42) |
| A1.2 | B1.8 | (C43) |
| A1.2 | B1.8 | (C51) |
| A1.2 | B1.8 | (C52) |
| A1.2 | B1.8 | (C57) |
| A1.2 | B1.8 | (C58) |
| A1.2 | B1.8 | (C59) |
| A1.2 | B1.8 | (C60) |
| A1.2 | B1.8 | (C61) |
| A1.2 | B1.8 | (C62) |
| A1.2 | B1.8 | (C65) |
| A1.2 | B1.8 | (C66) |
| A1.2 | B1.8 | (C71) |
| A1.2 | B1.8 | (C74) |
| A1.2 | B1.9 | (C1) |
| A1.2 | B1.9 | (C2) |
| A1.2 | B1.9 | (C3) |
| A1.2 | B1.9 | (C4) |
| A1.2 | B1.9 | (C5) |
| A1.2 | B1.9 | (C7) |
| A1.2 | B1.9 | (C9) |
| A1.2 | B1.9 | (C12) |
| A1.2 | B1.9 | (C13) |
| A1.2 | B1.9 | (C15) |
| A1.2 | B1.9 | (C18) |
| A1.2 | B1.9 | (C21) |
| A1.2 | B1.9 | (C22) |
| A1.2 | B1.9 | (C23) |
| A1.2 | B1.9 | (C24) |
| A1.2 | B1.9 | (C25) |
| A1.2 | B1.9 | (C28) |
| A1.2 | B1.9 | (C32) |
| A1.2 | B1.9 | (C37) |
| A1.2 | B1.9 | (C40) |
| A1.2 | B1.9 | (C41) |
| A1.2 | B1.9 | (C42) |
| A1.2 | B1.9 | (C43) |
| A1.2 | B1.9 | (C51) |
| A1.2 | B1.9 | (C52) |
| A1.2 | B1.9 | (C57) |
| A1.2 | B1.9 | (C58) |
| A1.2 | B1.9 | (C59) |
| A1.2 | B1.9 | (C60) |
| A1.2 | B1.9 | (C61) |
| A1.2 | B1.9 | (C62) |
| A1.2 | B1.9 | (C65) |
| A1.2 | B1.9 | (C66) |
| A1.2 | B1.9 | (C71) |
| A1.2 | B1.9 | (C74) |
| A1.2 | B1.10 | (C1) |
| A1.2 | B1.10 | (C2) |
| A1.2 | B1.10 | (C3) |
| A1.2 | B1.10 | (C4) |
| A1.2 | B1.10 | (C5) |
| A1.2 | B1.10 | (C7) |
| A1.2 | B1.10 | (C9) |
| A1.2 | B1.10 | (C12) |
| A1.2 | B1.10 | (C13) |
| A1.2 | B1.10 | (C15) |
| A1.2 | B1.10 | (C18) |
| A1.2 | B1.10 | (C21) |
| A1.2 | B1.10 | (C22) |
| A1.2 | B1.10 | (C23) |
| A1.2 | B1.10 | (C24) |
| A1.2 | B1.10 | (C25) |
| A1.2 | B1.10 | (C28) |
| A1.2 | B1.10 | (C32) |
| A1.2 | B1.10 | |
| A1.2 | B1.10 | (C40) |
| A1.2 | B1.10 | (C41) |

TABLE 2-continued

| Active compound (A) | Active compound (B) | Active compound (C) |
|---|---|---|
| A1.2 | B1.10 | (C42) |
| A1.2 | B1.10 | (C43) |
| A1.2 | B1.10 | (C51) |
| A1.2 | B1.10 | (C52) |
| A1.2 | B1.10 | (C57) |
| A1.2 | B1.10 | (C58) |
| A1.2 | B1.10 | (C59) |
| A1.2 | B1.10 | (C60) |
| A1.2 | B1.10 | (C61) |
| A1.2 | B1.10 | (C62) |
| A1.2 | B1.10 | (C65) |
| A1.2 | B1.10 | (C66) |
| A1.2 | B1.10 | (C71) |
| A1.2 | B1.10 | (C74) |
| A1.2 | B1.11 | (C1) |
| A1.2 | B1.11 | (C2) |
| A1.2 | B1.11 | (C3) |
| A1.2 | B1.11 | (C4) |
| A1.2 | B1.11 | (C5) |
| A1.2 | B1.11 | (C7) |
| A1.2 | B1.11 | (C9) |
| A1.2 | B1.11 | (C12) |
| A1.2 | B1.11 | (C13) |
| A1.2 | B1.11 | (C15) |
| A1.2 | B1.11 | (C18) |
| A1.2 | B1.11 | (C21) |
| A1.2 | B1.11 | (C22) |
| A1.2 | B1.11 | (C23) |
| A1.2 | B1.11 | (C24) |
| A1.2 | B1.11 | (C28) |
| A1.2 | B1.11 | (C32) |
| A1.2 | B1.11 | (C37) |
| A1.2 | B1.11 | (C40) |
| A1.2 | B1.11 | (C41) |
| A1.2 | B1.11 | (C42) |
| A1.2 | B1.11 | (C43) |
| A1.2 | B1.11 | (C51) |
| A1.2 | B1.11 | (C52) |
| A1.2 | B1.11 | (C57) |
| A1.2 | B1.11 | (C58) |
| A1.2 | B1.11 | (C59) |
| A1.2 | B1.11 | (C60) |
| A1.2 | B1.11 | (C61) |
| A1.2 | B1.11 | (C62) |
| A1.2 | B1.11 | (C65) |
| A1.2 | B1.11 | (C66) |
| A1.2 | B1.11 | (C71) |
| A1.2 | B1.11 | (C74) |
| A1.2 | B1.12 | (C1) |
| A1.2 | B1.12 | (C2) |
| A1.2 | B1.12 | (C3) |
| A1.2 | B1.12 | (C4) |
| A1.2 | B1.12 | (C5) |
| A1.2 | B1.12 | (C7) |
| A1.2 | B1.12 | (C9) |
| A1.2 | B1.12 | (C12) |
| A1.2 | B1.12 | (C13) |
| A1.2 | B1.12 | (C15) |
| A1.2 | B1.12 | (C18) |
| A1.2 | B1.12 | (C21) |
| A1.2 | B1.12 | (C22) |
| A1.2 | B1.12 | (C23) |
| A1.2 | B1.12 | (C24) |
| A1.2 | B1.12 | (C25) |
| A1.2 | B1.12 | (C28) |
| A1.2 | B1.12 | (C32) |
| A1.2 | B1.12 | (C37) |
| A1.2 | B1.12 | (C40) |
| A1.2 | B1.12 | (C41) |
| A1.2 | B1.12 | (C42) |
| A1.2 | B1.12 | (C43) |
| A1.2 | B1.12 | (C51) |
| A1.2 | B1.12 | (C52) |
| A1.2 | B1.12 | (C57) |
| A1.2 | B1.12 | (C58) |
| A1.2 | B1.12 | (C59) |
| A1.2 | B1.12 | (C60) |
| A1.2 | B1.12 | (C61) |
| A1.2 | B1.12 | (C62) |
| A1.2 | B1.12 | (C62) |
| A1.2 | B1.12 | (C65) |
| A1.2 | B1.12 | (C66) |
| A1.2 | B1.12 | (C71) |
| A1.2 | B1.12 | (C74) |
| A1.2 | B1.13 | (C1) |
| A1.2 | B1.13 | (C2) |
| A1.2 | B1.13 | (C3) |
| A1.2 | B1.13 | (C4) |
| A1.2 | B1.13 | (C5) |
| A1.2 | B1.13 | (C7) |
| A1.2 | B1.13 | (C9) |
| A1.2 | B1.13 | (C12) |
| A1.2 | B1.13 | (C13) |
| A1.2 | B1.13 | (C15) |
| A1.2 | B1.13 | (C18) |
| A1.2 | B1.13 | (C21) |
| A1.2 | B1.13 | (C22) |
| A1.2 | B1.13 | (C23) |
| A1.2 | B1.13 | (C24) |
| A1.2 | B1.13 | (C25) |
| A1.2 | B1.13 | (C28) |
| A1.2 | B1.13 | (C32) |
| A1.2 | B1.13 | (C37) |
| A1.2 | B1.13 | (C40) |
| A1.2 | B1.13 | (C41) |
| A1.2 | B1.13 | (C42) |
| A1.2 | B1.13 | (C43) |
| A1.2 | B1.13 | (C51) |
| A1.2 | B1.13 | (C52) |
| A1.2 | B1.13 | (C57) |
| A1.2 | B1.13 | (C58) |
| A1.2 | B1.13 | (C59) |
| A1.2 | B1.13 | (C60) |
| A1.2 | B1.13 | (C61) |
| A1.2 | B1.13 | (C62) |
| A1.2 | B1.13 | (C65) |
| A1.2 | B1.13 | (C66) |
| A1.2 | B1.13 | (C71) |
| A1.2 | B1.13 | (C74) |
| A1.2 | B1.14 | (C1) |
| A1.2 | B1.14 | (C2) |
| A1.2 | B1.14 | (C3) |
| A1.2 | B1.14 | (C4) |
| A1.2 | B1.14 | (C5) |
| A1.2 | B1.14 | (C7) |
| A1.2 | B1.14 | (C9) |
| A1.2 | B1.14 | (C12) |
| A1.2 | B1.14 | (C13) |
| A1.2 | B1.14 | (C15) |
| A1.2 | B1.14 | (C18) |
| A1.2 | B1.14 | (C21) |
| A1.2 | B1.14 | (C22) |
| A1.2 | B1.14 | (C23) |
| A1.2 | B1.14 | (C24) |
| A1.2 | B1.14 | (C25) |
| A1.2 | B1.14 | (C28) |
| A1.2 | B1.14 | (C32) |
| A1.2 | B1.14 | (C37) |
| A1.2 | B1.14 | (C40) |
| A1.2 | B1.14 | (C41) |
| A1.2 | B1.14 | (C42) |
| A1.2 | B1.14 | (C43) |
| A1.2 | B1.14 | (C51) |
| A1.2 | B1.14 | (C52) |
| A1.2 | B1.14 | (C57) |
| A1.2 | B1.14 | (C58) |
| A1.2 | B1.14 | (C59) |
| A1.2 | B1.14 | (C60) |
| A1.2 | B1.14 | (C61) |
| A1.2 | B1.14 | (C62) |
| A1.2 | B1.14 | (C65) |
| A1.2 | B1.14 | (C66) |

TABLE 2-continued

| Active compound (A) | Active compound (B) | Active compound (C) |
|---|---|---|
| A1.2 | B1.14 | (C71) |
| A1.2 | B1.14 | (C74) |
| A1.2 | B1.15 | (C1) |
| A1.2 | B1.15 | (C2) |
| A1.2 | B1.15 | (C3) |
| A1.2 | B1.15 | (C4) |
| A1.2 | B1.15 | (C5) |
| A1.2 | B1.15 | (C7) |
| A1.2 | B1.15 | (C9) |
| A1.2 | B1.15 | (C12) |
| A1.2 | B1.15 | (C13) |
| A1.2 | B1.15 | (C15) |
| A1.2 | B1.15 | (C18) |
| A1.2 | B1.15 | (C21) |
| A1.2 | B1.15 | (C22) |
| A1.2 | B1.15 | (C23) |
| A1.2 | B1.15 | (C24) |
| A1.2 | B1.15 | (C25) |
| A1.2 | B1.15 | (C28) |
| A1.2 | B1.15 | (C32) |
| A1.2 | B1.15 | (C37) |
| A1.2 | B1.15 | (C40) |
| A1.2 | B1.15 | (C41) |
| A1.2 | B1.15 | (C42) |
| A1.2 | B1.15 | (C43) |
| A1.2 | B1.15 | (C51) |
| A1.2 | B1.15 | (C52) |
| A1.2 | B1.15 | (C57) |
| A1.2 | B1.15 | (C58) |
| A1.2 | B1.15 | (C59) |
| A1.2 | B1.15 | (C60) |
| A1.2 | B1.15 | (C61) |
| A1.2 | B1.15 | (C62) |
| A1.2 | B1.15 | (C65) |
| A1.2 | B1.15 | (C66) |
| A1.2 | B1.15 | (C71) |
| A1.2 | B1.15 | (C74) |
| A1.2 | B1.16 | (C1) |
| A1.2 | B1.16 | (C2) |
| A1.2 | B1.16 | (C3) |
| A1.2 | B1.16 | (C4) |
| A1.2 | B1.16 | (C5) |
| A1.2 | B1.16 | (C7) |
| A1.2 | B1.16 | (C9) |
| A1.2 | B1.16 | (C12) |
| A1.2 | B1.16 | (C13) |
| A1.2 | B1.16 | (C15) |
| A1.2 | B1.16 | (C18) |
| A1.2 | B1.16 | (C21) |
| A1.2 | B1.16 | (C22) |
| A1.2 | B1.16 | (C23) |
| A1.2 | B1.16 | (C24) |
| A1.2 | B1.16 | (C25) |
| A1.2 | B1.16 | (C28) |
| A1.2 | B1.16 | (C32) |
| A1.2 | B1.16 | (C37) |
| A1.2 | B1.16 | (C40) |
| A1.2 | B1.16 | (C41) |
| A1.2 | B1.16 | (C42) |
| A1.2 | B1.16 | (C43) |
| A1.2 | B1.16 | (C51) |
| A1.2 | B1.16 | (C52) |
| A1.2 | B1.16 | (C57) |
| A1.2 | B1.16 | (C58) |
| A1.2 | B1.16 | (C59) |
| A1.2 | B1.16 | (C60) |
| A1.2 | B1.16 | (C61) |
| A1.2 | B1.16 | (C62) |
| A1.2 | B1.16 | (C65) |
| A1.2 | B1.16 | (C66) |
| A1.2 | B1.16 | (C71) |
| A1.2 | B1.16 | (C74) |
| A1.2 | B1.17 | (C1) |
| A1.2 | B1.17 | (C2) |
| A1.2 | B1.17 | (C3) |
| A1.2 | B1.17 | (C4) |
| A1.2 | B1.17 | (C5) |
| A1.2 | B1.17 | (C7) |
| A1.2 | B1.17 | (C9) |
| A1.2 | B1.17 | (C12) |
| A1.2 | B1.17 | (C13) |
| A1.2 | B1.17 | (C15) |
| A1.2 | B1.17 | (C18) |
| A1.2 | B1.17 | (C21) |
| A1.2 | B1.17 | (C22) |
| A1.2 | B1.17 | (C23) |
| A1.2 | B1.17 | (C24) |
| A1.2 | B1.17 | (C25) |
| A1.2 | B1.17 | (C28) |
| A1.2 | B1.17 | (C32) |
| A1.2 | B1.17 | (C37) |
| A1.2 | B1.17 | (C40) |
| A1.2 | B1.17 | (C41) |
| A1.2 | B1.17 | (C42) |
| A1.2 | B1.17 | (C43) |
| A1.2 | B1.17 | (C51) |
| A1.2 | B1.17 | (C52) |
| A1.2 | B1.17 | (C57) |
| A1.2 | B1.17 | (C58) |
| A1.2 | B1.17 | (C59) |
| A1.2 | B1.17 | (C60) |
| A1.2 | B1.17 | (C61) |
| A1.2 | B1.17 | (C62) |
| A1.2 | B1.17 | (C65) |
| A1.2 | B1.17 | (C66) |
| A1.2 | B1.17 | (C71) |
| A1.2 | B1.17 | (C74) |
| A1.2 | B1.18 | (C1) |
| A1.2 | B1.18 | (C2) |
| A1.2 | B1.18 | (C3) |
| A1.2 | B1.18 | (C4) |
| A1.2 | B1.18 | (C5) |
| A1.2 | B1.18 | (C7) |
| A1.2 | B1.18 | (C9) |
| A1.2 | B1.18 | (C12) |
| A1.2 | B1.18 | (C13) |
| A1.2 | B1.18 | (C15) |
| A1.2 | B1.18 | (C18) |
| A1.2 | B1.18 | (C21) |
| A1.2 | B1.18 | (C22) |
| A1.2 | B1.18 | (C23) |
| A1.2 | B1.18 | (C24) |
| A1.2 | B1.18 | (C25) |
| A1.2 | B1.18 | (C28) |
| A1.2 | B1.18 | (C32) |
| A1.2 | B1.18 | (C37) |
| A1.2 | B1.18 | (C40) |
| A1.2 | B1.18 | (C41) |
| A1.2 | B1.18 | (C42) |
| A1.2 | B1.18 | (C43) |
| A1.2 | B1.18 | (C51) |
| A1.2 | B1.18 | (C52) |
| A1.2 | B1.18 | (C57) |
| A1.2 | B1.18 | (C58) |
| A1.2 | B1.18 | (C59) |
| A1.2 | B1.18 | (C60) |
| A1.2 | B1.18 | (C61) |
| A1.2 | B1.18 | (C62) |
| A1.2 | B1.18 | (C65) |
| A1.2 | B1.18 | (C66) |
| A1.2 | B1.18 | (C71) |
| A1.2 | B1.18 | (C74) |
| A1.2 | B1.19 | (C1) |
| A1.2 | B1.19 | (C2) |
| A1.2 | B1.19 | (C3) |
| A1.2 | B1.19 | (C4) |
| A1.2 | B1.19 | (C5) |
| A1.2 | B1.19 | (C7) |
| A1.2 | B1.19 | (C9) |
| A1.2 | B1.19 | (C12) |
| A1.2 | B1.19 | (C13) |
| A1.2 | B1.19 | (C15) |

TABLE 2-continued

| Active compound (A) | Active compound (B) | Active compound (C) |
|---|---|---|
| A1.2 | B1.19 | (C18) |
| A1.2 | B1.19 | (C21) |
| A1.2 | B1.19 | (C22) |
| A1.2 | B1.19 | (C23) |
| A1.2 | B1.19 | (C24) |
| A1.2 | B1.19 | (C25) |
| A1.2 | B1.19 | (C25) |
| A1.2 | B1.19 | (C28) |
| A1.2 | B1.19 | (C32) |
| A1.2 | B1.19 | (C37) |
| A1.2 | B1.19 | (C40) |
| A1.2 | B1.19 | (C41) |
| A1.2 | B1.19 | (C42) |
| A1.2 | B1.19 | (C43) |
| A1.2 | B1.19 | (C51) |
| A1.2 | B1.19 | (C52) |
| A1.2 | B1.19 | (C57) |
| A1.2 | B1.19 | (C58) |
| A1.2 | B1.19 | (C59) |
| A1.2 | B1.19 | (C60) |
| A1.2 | B1.19 | (C61) |
| A1.2 | B1.19 | (C62) |
| A1.2 | B1.19 | (C65) |
| A1.2 | B1.19 | (C66) |
| A1.2 | B1.19 | (C71) |
| A1.2 | B1.19 | (C74) |
| A1.2 | B1.20 | (C1) |
| A1.2 | B1.20 | (C2) |
| A1.2 | B1.20 | (C3) |
| A1.2 | B1.20 | (C4) |
| A1.2 | B1.20 | (C5) |
| A1.2 | B1.20 | (C7) |
| A1.2 | B1.20 | (C9) |
| A1.2 | B1.20 | (C12) |
| A1.2 | B1.20 | (C13) |
| A1.2 | B1.20 | (C15) |
| A1.2 | B1.20 | (C18) |
| A1.2 | B1.20 | (C21) |
| A1.2 | B1.20 | (C22) |
| A1.2 | B1.20 | (C23) |
| A1.2 | B1.20 | (C24) |
| A1.2 | B1.20 | (C25) |
| A1.2 | B1.20 | (C25) |
| A1.2 | B1.20 | (C28) |
| A1.2 | B1.20 | (C32) |
| A1.2 | B1.20 | (C37) |
| A1.2 | B1.20 | (C40) |
| A1.2 | B1.20 | (C41) |
| A1.2 | B1.20 | (C42) |
| A1.2 | B1.20 | (C43) |
| A1.2 | B1.20 | (C51) |
| A1.2 | B1.20 | (C52) |
| A1.2 | B1.20 | (C57) |
| A1.2 | B1.20 | (C58) |
| A1.2 | B1.20 | (C59) |
| A1.2 | B1.20 | (C60) |
| A1.2 | B1.20 | (C61) |
| A1.2 | B1.20 | (C62) |
| A1.2 | B1.20 | (C65) |
| A1.2 | B1.20 | (C66) |
| A1.2 | B1.20 | (C71) |
| A1.2 | B1.20 | (C74) |
| A1.2 | B1.21 | (C1) |
| A1.2 | B1.21 | (C2) |
| A1.2 | B1.21 | (C3) |
| A1.2 | B1.21 | (C4) |
| A1.2 | B1.21 | (C5) |
| A1.2 | B1.21 | (C7) |
| A1.2 | B1.21 | (C9) |
| A1.2 | B1.21 | (C12) |
| A1.2 | B1.21 | (C13) |
| A1.2 | B1.21 | (C15) |
| A1.2 | B1.21 | (C18) |
| A1.2 | B1.21 | (C21) |
| A1.2 | B1.21 | (C22) |
| A1.2 | B1.21 | (C23) |
| A1.2 | B1.21 | (C24) |
| A1.2 | B1.21 | (C25) |
| A1.2 | B1.21 | (C25) |
| A1.2 | B1.21 | (C28) |
| A1.2 | B1.21 | (C32) |
| A1.2 | B1.21 | (C37) |
| A1.2 | B1.21 | (C40) |
| A1.2 | B1.21 | (C41) |
| A1.2 | B1.21 | (C42) |
| A1.2 | B1.21 | (C43) |
| A1.2 | B1.21 | (C51) |
| A1.2 | B1.21 | (C52) |
| A1.2 | B1.21 | (C57) |
| A1.2 | B1.21 | (C58) |
| A1.2 | B1.21 | (C59) |
| A1.2 | B1.21 | (C60) |
| A1.2 | B1.21 | (C61) |
| A1.2 | B1.21 | (C62) |
| A1.2 | B1.21 | (C65) |
| A1.2 | B1.21 | (C66) |
| A1.2 | B1.21 | (C71) |
| A1.2 | B1.21 | (C74) |
| A1.2 | B1.22 | (C1) |
| A1.2 | B1.22 | (C2) |
| A1.2 | B1.22 | (C3) |
| A1.2 | B1.22 | (C4) |
| A1.2 | B1.22 | (C5) |
| A1.2 | B1.22 | (C7) |
| A1.2 | B1.22 | (C9) |
| A1.2 | B1.22 | (C12) |
| A1.2 | B1.22 | (C13) |
| A1.2 | B1.22 | (C15) |
| A1.2 | B1.22 | (C18) |
| A1.2 | B1.22 | (C21) |
| A1.2 | B1.22 | (C22) |
| A1.2 | B1.22 | (C23) |
| A1.2 | B1.22 | (C24) |
| A1.2 | B1.22 | (C25) |
| A1.2 | B1.22 | (C25) |
| A1.2 | B1.22 | (C28) |
| A1.2 | B1.22 | (C32) |
| A1.2 | B1.22 | (C37) |
| A1.2 | B1.22 | (C40) |
| A1.2 | B1.22 | (C41) |
| A1.2 | B1.22 | (C42) |
| A1.2 | B1.22 | (C43) |
| A1.2 | B1.22 | (C51) |
| A1.2 | B1.22 | (C52) |
| A1.2 | B1.22 | (C57) |
| A1.2 | B1.22 | (C58) |
| A1.2 | B1.22 | (C59) |
| A1.2 | B1.22 | (C60) |
| A1.2 | B1.22 | (C61) |
| A1.2 | B1.22 | (C62) |
| A1.2 | B1.22 | (C65) |
| A1.2 | B1.22 | (C66) |
| A1.2 | B1.22 | (C71) |
| A1.2 | B1.22 | (C74) |
| A1.2 | B1.23 | (C1) |
| A1.2 | B1.23 | (C2) |
| A1.2 | B1.23 | (C3) |
| A1.2 | B1.23 | (C4) |
| A1.2 | B1.23 | (C5) |
| A1.2 | B1.23 | (C7) |
| A1.2 | B1.23 | (C9) |
| A1.2 | B1.23 | (C12) |
| A1.2 | B1.23 | (C13) |
| A1.2 | B1.23 | (C15) |
| A1.2 | B1.23 | (C18) |
| A1.2 | B1.23 | (C21) |
| A1.2 | B1.23 | (C22) |
| A1.2 | B1.23 | (C23) |
| A1.2 | B1.23 | (C24) |
| A1.2 | B1.23 | (C25) |
| A1.2 | B1.23 | (C25) |
| A1.2 | B1.23 | (C28) |

TABLE 2-continued

| Active compound (A) | Active compound (B) | Active compound (C) |
|---|---|---|
| A1.2 | B1.23 | (C32) |
| A1.2 | B1.23 | (C37) |
| A1.2 | B1.23 | (C40) |
| A1.2 | B1.23 | (C41) |
| A1.2 | B1.23 | (C42) |
| A1.2 | B1.23 | (C43) |
| A1.2 | B1.23 | (C51) |
| A1.2 | B1.23 | (C52) |
| A1.2 | B1.23 | (C57) |
| A1.2 | B1.23 | (C58) |
| A1.2 | B1.23 | (C59) |
| A1.2 | B1.23 | (C60) |
| A1.2 | B1.23 | (C61) |
| A1.2 | B1.23 | (C62) |
| A1.2 | B1.23 | (C65) |
| A1.2 | B1.23 | (C66) |
| A1.2 | B1.23 | (C71) |
| A1.2 | B1.23 | (C74) |
| A1.3 | B1.0 | (C1) |
| A1.3 | B1.0 | (C2) |
| A1.3 | B1.0 | (C3) |
| A1.3 | B1.0 | (C4) |
| A1.3 | B1.0 | (C5) |
| A1.3 | B1.0 | (C7) |
| A1.3 | B1.0 | (C9) |
| A1.3 | B1.0 | (C12) |
| A1.3 | B1.0 | (C13) |
| A1.3 | B1.0 | (C15) |
| A1.3 | B1.0 | (C18) |
| A1.3 | B1.0 | (C21) |
| A1.3 | B1.0 | (C22) |
| A1.3 | B1.0 | (C23) |
| A1.3 | B1.0 | (C24) |
| A1.3 | B1.0 | (C25) |
| A1.3 | B1.0 | (C25) |
| A1.3 | B1.0 | (C28) |
| A1.3 | B1.0 | (C32) |
| A1.3 | B1.0 | (C37) |
| A1.3 | B1.0 | (C40) |
| A1.3 | B1.0 | (C41) |
| A1.3 | B1.0 | (C42) |
| A1.3 | B1.0 | (C43) |
| A1.3 | B1.0 | (C51) |
| A1.3 | B1.0 | (C52) |
| A1.3 | B1.0 | (C57) |
| A1.3 | B1.0 | (C58) |
| A1.3 | B1.0 | (C59) |
| A1.3 | B1.0 | (C60) |
| A1.3 | B1.0 | (C61) |
| A1.3 | B1.0 | (C62) |
| A1.3 | B1.0 | (C65) |
| A1.3 | B1.0 | (C66) |
| A1.3 | B1.0 | (C71) |
| A1.3 | B1.0 | (C74) |
| A1.3 | B1.1 | (C1) |
| A1.3 | B1.1 | (C2) |
| A1.3 | B1.1 | (C3) |
| A1.3 | B1.1 | (C4) |
| A1.3 | B1.1 | (C5) |
| A1.3 | B1.1 | (C7) |
| A1.3 | B1.1 | (C9) |
| A1.3 | B1.1 | (C12) |
| A1.3 | B1.1 | (C13) |
| A1.3 | B1.1 | (C15) |
| A1.3 | B1.1 | (C18) |
| A1.3 | B1.1 | (C21) |
| A1.3 | B1.1 | (C22) |
| A1.3 | B1.1 | (C23) |
| A1.3 | B1.1 | (C24) |
| A1.3 | B1.1 | (C25) |
| A1.3 | B1.1 | (C28) |
| A1.3 | B1.1 | (C32) |
| A1.3 | B1.1 | (C37) |
| A1.3 | B1.1 | (C40) |
| A1.3 | B1.1 | (C41) |
| A1.3 | B1.1 | (C42) |
| A1.3 | B1.1 | (C43) |
| A1.3 | B1.1 | (C51) |
| A1.3 | B1.1 | (C52) |
| A1.3 | B1.1 | (C57) |
| A1.3 | B1.1 | (C58) |
| A1.3 | B1.1 | (C59) |
| A1.3 | B1.1 | (C60) |
| A1.3 | B1.1 | (C61) |
| A1.3 | B1.1 | (C62) |
| A1.3 | B1.1 | (C65) |
| A1.3 | B1.1 | (C66) |
| A1.3 | B1.1 | (C71) |
| A1.3 | B1.1 | (C74) |
| A1.3 | B1.2 | (C1) |
| A1.3 | B1.2 | (C2) |
| A1.3 | B1.2 | (C3) |
| A1.3 | B1.2 | (C4) |
| A1.3 | B1.2 | (C5) |
| A1.3 | B1.2 | (C7) |
| A1.3 | B1.2 | (C9) |
| A1.3 | B1.2 | (C12) |
| A1.3 | B1.2 | (C13) |
| A1.3 | B1.2 | (C15) |
| A1.3 | B1.2 | (C18) |
| A1.3 | B1.2 | (C21) |
| A1.3 | B1.2 | (C22) |
| A1.3 | B1.2 | (C23) |
| A1.3 | B1.2 | (C24) |
| A1.3 | B1.2 | (C25) |
| A1.3 | B1.2 | (C28) |
| A1.3 | B1.2 | (C32) |
| A1.3 | B1.2 | (C37) |
| A1.3 | B1.2 | (C40) |
| A1.3 | B1.2 | (C41) |
| A1.3 | B1.2 | (C42) |
| A1.3 | B1.2 | (C43) |
| A1.3 | B1.2 | (C51) |
| A1.3 | B1.2 | (C52) |
| A1.3 | B1.2 | (C57) |
| A1.3 | B1.2 | (C58) |
| A1.3 | B1.2 | (C59) |
| A1.3 | B1.2 | (C60) |
| A1.3 | B1.2 | (C61) |
| A1.3 | B1.2 | (C62) |
| A1.3 | B1.2 | (C65) |
| A1.3 | B1.2 | (C66) |
| A1.3 | B1.2 | (C71) |
| A1.3 | B1.2 | (C74) |
| A1.3 | B1.3 | (C1) |
| A1.3 | B1.3 | (C2) |
| A1.3 | B1.3 | (C3) |
| A1.3 | B1.3 | (C4) |
| A1.3 | B1.3 | (C5) |
| A1.3 | B1.3 | (C7) |
| A1.3 | B1.3 | (C9) |
| A1.3 | B1.3 | (C12) |
| A1.3 | B1.3 | (C13) |
| A1.3 | B1.3 | (C15) |
| A1.3 | B1.3 | (C18) |
| A1.3 | B1.3 | (C21) |
| A1.3 | B1.3 | (C22) |
| A1.3 | B1.3 | (C23) |
| A1.3 | B1.3 | (C24) |
| A1.3 | B1.3 | (C25) |
| A1.3 | B1.3 | (C28) |
| A1.3 | B1.3 | (C32) |
| A1.3 | B1.3 | (C37) |
| A1.3 | B1.3 | (C40) |
| A1.3 | B1.3 | (C41) |
| A1.3 | B1.3 | (C42) |
| A1.3 | B1.3 | (C43) |
| A1.3 | B1.3 | (C51) |
| A1.3 | B1.3 | (C52) |
| A1.3 | B1.3 | (C57) |
| A1.3 | B1.3 | (C58) |
| A1.3 | B1.3 | (C59) |

TABLE 2-continued

| Active compound (A) | Active compound (B) | Active compound (C) |
|---|---|---|
| A1.3 | B1.3 | (C60) |
| A1.3 | B1.3 | (C61) |
| A1.3 | B1.3 | (C62) |
| A1.3 | B1.3 | (C65) |
| A1.3 | B1.3 | (C66) |
| A1.3 | B1.3 | (C71) |
| A1.3 | B1.3 | (C74) |
| A1.3 | B1.4 | (C1) |
| A1.3 | B1.4 | (C2) |
| A1.3 | B1.4 | (C3) |
| A1.3 | B1.4 | (C4) |
| A1.3 | B1.4 | (C5) |
| A1.3 | B1.4 | (C7) |
| A1.3 | B1.4 | (C9) |
| A1.3 | B1.4 | (C12) |
| A1.3 | B1.4 | (C13) |
| A1.3 | B1.4 | (C15) |
| A1.3 | B1.4 | (C18) |
| A1.3 | B1.4 | (C21) |
| A1.3 | B1.4 | (C22) |
| A1.3 | B1.4 | (C23) |
| A1.3 | B1.4 | (C24) |
| A1.3 | B1.4 | (C25) |
| A1.3 | B1.4 | (C28) |
| A1.3 | B1.4 | (C32) |
| A1.3 | B1.4 | (C37) |
| A1.3 | B1.4 | (C40) |
| A1.3 | B1.4 | (C41) |
| A1.3 | B1.4 | (C42) |
| A1.3 | B1.4 | (C43) |
| A1.3 | B1.4 | (C51) |
| A1.3 | B1.4 | (C52) |
| A1.3 | B1.4 | (C57) |
| A1.3 | B1.4 | (C58) |
| A1.3 | B1.4 | (C59) |
| A1.3 | B1.4 | (C60) |
| A1.3 | B1.4 | (C61) |
| A1.3 | B1.4 | (C62) |
| A1.3 | B1.4 | (C65) |
| A1.3 | B1.4 | (C66) |
| A1.3 | B1.4 | (C71) |
| A1.3 | B1.4 | (C74) |
| A1.3 | B1.5 | (C1) |
| A1.3 | B1.5 | (C2) |
| A1.3 | B1.5 | (C3) |
| A1.3 | B1.5 | (C4) |
| A1.3 | B1.5 | (C5) |
| A1.3 | B1.5 | (C7) |
| A1.3 | B1.5 | (C9) |
| A1.3 | B1.5 | (C12) |
| A1.3 | B1.5 | (C13) |
| A1.3 | B1.5 | (C15) |
| A1.3 | B1.5 | (C18) |
| A1.3 | B1.5 | (C21) |
| A1.3 | B1.5 | (C22) |
| A1.3 | B1.5 | (C23) |
| A1.3 | B1.5 | (C24) |
| A1.3 | B1.5 | (C25) |
| A1.3 | B1.5 | (C28) |
| A1.3 | B1.5 | (C32) |
| A1.3 | B1.5 | (C37) |
| A1.3 | B1.5 | (C40) |
| A1.3 | B1.5 | (C41) |
| A1.3 | B1.5 | (C42) |
| A1.3 | B1.5 | (C43) |
| A1.3 | B1.5 | (C51) |
| A1.3 | B1.5 | (C52) |
| A1.3 | B1.5 | (C57) |
| A1.3 | B1.5 | (C58) |
| A1.3 | B1.5 | (C59) |
| A1.3 | B1.5 | (C60) |
| A1.3 | B1.5 | (C61) |
| A1.3 | B1.5 | (C62) |
| A1.3 | B1.5 | (C62) |
| A1.3 | B1.5 | (C65) |
| A1.3 | B1.5 | (C66) |
| A1.3 | B1.5 | (C71) |
| A1.3 | B1.5 | (C74) |
| A1.3 | B1.6 | (C1) |
| A1.3 | B1.6 | (C2) |
| A1.3 | B1.6 | (C3) |
| A1.3 | B1.6 | (C4) |
| A1.3 | B1.6 | (C5) |
| A1.3 | B1.6 | (C7) |
| A1.3 | B1.6 | (C9) |
| A1.3 | B1.6 | (C12) |
| A1.3 | B1.6 | (C13) |
| A1.3 | B1.6 | (C15) |
| A1.3 | B1.6 | (C18) |
| A1.3 | B1.6 | (C21) |
| A1.3 | B1.6 | (C22) |
| A1.3 | B1.6 | (C23) |
| A1.3 | B1.6 | (C24) |
| A1.3 | B1.6 | (C25) |
| A1.3 | B1.6 | (C28) |
| A1.3 | B1.6 | (C32) |
| A1.3 | B1.6 | (C37) |
| A1.3 | B1.6 | (C40) |
| A1.3 | B1.6 | (C41) |
| A1.3 | B1.6 | (C42) |
| A1.3 | B1.6 | (C43) |
| A1.3 | B1.6 | (C51) |
| A1.3 | B1.6 | (C52) |
| A1.3 | B1.6 | (C57) |
| A1.3 | B1.6 | (C58) |
| A1.3 | B1.6 | (C57) |
| A1.3 | B1.6 | (C58) |
| A1.3 | B1.6 | (C59) |
| A1.3 | B1.6 | (C60) |
| A1.3 | B1.6 | (C61) |
| A1.3 | B1.6 | (C62) |
| A1.3 | B1.6 | (C62) |
| A1.3 | B1.6 | (C65) |
| A1.3 | B1.6 | (C66) |
| A1.3 | B1.6 | (C71) |
| A1.3 | B1.6 | (C74) |
| A1.3 | B1.7 | (C1) |
| A1.3 | B1.7 | (C2) |
| A1.3 | B1.7 | (C3) |
| A1.3 | B1.7 | (C4) |
| A1.3 | B1.7 | (C5) |
| A1.3 | B1.7 | (C7) |
| A1.3 | B1.7 | (C9) |
| A1.3 | B1.7 | (C12) |
| A1.3 | B1.7 | (C13) |
| A1.3 | B1.7 | (C15) |
| A1.3 | B1.7 | (C18) |
| A1.3 | B1.7 | (C21) |
| A1.3 | B1.7 | (C22) |
| A1.3 | B1.7 | (C23) |
| A1.3 | B1.7 | (C24) |
| A1.3 | B1.7 | (C25) |
| A1.3 | B1.7 | (C28) |
| A1.3 | B1.7 | (C32) |
| A1.3 | B1.7 | (C37) |
| A1.3 | B1.7 | (C40) |
| A1.3 | B1.7 | (C41) |
| A1.3 | B1.7 | (C42) |
| A1.3 | B1.7 | (C43) |
| A1.3 | B1.7 | (C51) |
| A1.3 | B1.7 | (C52) |
| A1.3 | B1.7 | (C57) |
| A1.3 | B1.7 | (C58) |
| A1.3 | B1.7 | (C59) |
| A1.3 | B1.7 | (C60) |
| A1.3 | B1.7 | (C61) |
| A1.3 | B1.7 | (C62) |
| A1.3 | B1.7 | (C65) |
| A1.3 | B1.7 | (C66) |
| A1.3 | B1.7 | (C71) |
| A1.3 | B1.7 | (C74) |
| A1.3 | B1.8 | (C1) |

TABLE 2-continued

| Active compound (A) | Active compound (B) | Active compound (C) |
|---|---|---|
| A1.3 | B1.8 | (C2) |
| A1.3 | B1.8 | (C3) |
| A1.3 | B1.8 | (C4) |
| A1.3 | B1.8 | (C5) |
| A1.3 | B1.8 | (C7) |
| A1.3 | B1.8 | (C9) |
| A1.3 | B1.8 | (C12) |
| A1.3 | B1.8 | (C13) |
| A1.3 | B1.8 | (C15) |
| A1.3 | B1.8 | (C18) |
| A1.3 | B1.8 | (C21) |
| A1.3 | B1.8 | (C22) |
| A1.3 | B1.8 | (C23) |
| A1.3 | B1.8 | (C24) |
| A1.3 | B1.8 | (C25) |
| A1.3 | B1.8 | (C28) |
| A1.3 | B1.8 | (C32) |
| A1.3 | B1.8 | (C37) |
| A1.3 | B1.8 | (C40) |
| A1.3 | B1.8 | (C41) |
| A1.3 | B1.8 | (C42) |
| A1.3 | B1.8 | (C43) |
| A1.3 | B1.8 | (C43) |
| A1.3 | B1.8 | (C51) |
| A1.3 | B1.8 | (C52) |
| A1.3 | B1.8 | (C57) |
| A1.3 | B1.8 | (C58) |
| A1.3 | B1.8 | (C59) |
| A1.3 | B1.8 | (C60) |
| A1.3 | B1.8 | (C61) |
| A1.3 | B1.8 | (C62) |
| A1.3 | B1.8 | (C65) |
| A1.3 | B1.8 | (C66) |
| A1.3 | B1.8 | (C71) |
| A1.3 | B1.8 | (C74) |
| A1.3 | B1.9 | (C1) |
| A1.3 | B1.9 | (C2) |
| A1.3 | B1.9 | (C3) |
| A1.3 | B1.9 | (C4) |
| A1.3 | B1.9 | (C5) |
| A1.3 | B1.9 | (C7) |
| A1.3 | B1.9 | (C9) |
| A1.3 | B1.9 | (C12) |
| A1.3 | B1.9 | (C13) |
| A1.3 | B1.9 | (C15) |
| A1.3 | B1.9 | (C18) |
| A1.3 | B1.9 | (C21) |
| A1.3 | B1.9 | (C22) |
| A1.3 | B1.9 | (C23) |
| A1.3 | B1.9 | (C24) |
| A1.3 | B1.9 | (C25) |
| A1.3 | B1.9 | (C28) |
| A1.3 | B1.9 | (C32) |
| A1.3 | B1.9 | (C37) |
| A1.3 | B1.9 | (C40) |
| A1.3 | B1.9 | (C41) |
| A1.3 | B1.9 | (C42) |
| A1.3 | B1.9 | (C43) |
| A1.3 | B1.9 | (C51) |
| A1.3 | B1.9 | (C52) |
| A1.3 | B1.9 | (C57) |
| A1.3 | B1.9 | (C58) |
| A1.3 | B1.9 | (C59) |
| A1.3 | B1.9 | (C60) |
| A1.3 | B1.9 | (C61) |
| A1.3 | B1.9 | (C62) |
| A1.3 | B1.9 | (C65) |
| A1.3 | B1.9 | (C66) |
| A1.3 | B1.9 | (C71) |
| A1.3 | B1.9 | (C74) |
| A1.3 | B1.10 | (C1) |
| A1.3 | B1.10 | (C2) |
| A1.3 | B1.10 | (C3) |
| A1.3 | B1.10 | (C4) |
| A1.3 | B1.10 | (C5) |
| A1.3 | B1.10 | (C7) |
| A1.3 | B1.10 | (C9) |
| A1.3 | B1.10 | (C12) |
| A1.3 | B1.10 | (C13) |
| A1.3 | B1.10 | (C15) |
| A1.3 | B1.10 | (C18) |
| A1.3 | B1.10 | (C21) |
| A1.3 | B1.10 | (C22) |
| A1.3 | B1.10 | (C23) |
| A1.3 | B1.10 | (C24) |
| A1.3 | B1.10 | (C25) |
| A1.3 | B1.10 | (C28) |
| A1.3 | B1.10 | (C32) |
| A1.3 | B1.10 | (C37) |
| A1.3 | B1.10 | (C40) |
| A1.3 | B1.10 | (C41) |
| A1.3 | B1.10 | (C42) |
| A1.3 | B1.10 | (C43) |
| A1.3 | B1.10 | (C51) |
| A1.3 | B1.10 | (C52) |
| A1.3 | B1.10 | (C57) |
| A1.3 | B1.10 | (C58) |
| A1.3 | B1.10 | (C59) |
| A1.3 | B1.10 | (C60) |
| A1.3 | B1.10 | (C61) |
| A1.3 | B1.10 | (C62) |
| A1.3 | B1.10 | (C65) |
| A1.3 | B1.10 | (C66) |
| A1.3 | B1.10 | (C71) |
| A1.3 | B1.10 | (C74) |
| A1.3 | B1.11 | (C1) |
| A1.3 | B1.11 | (C2) |
| A1.3 | B1.11 | (C3) |
| A1.3 | B1.11 | (C4) |
| A1.3 | B1.11 | (C5) |
| A1.3 | B1.11 | (C7) |
| A1.3 | B1.11 | (C9) |
| A1.3 | B1.11 | (C12) |
| A1.3 | B1.11 | (C13) |
| A1.3 | B1.11 | (C15) |
| A1.3 | B1.11 | (C18) |
| A1.3 | B1.11 | (C21) |
| A1.3 | B1.11 | (C22) |
| A1.3 | B1.11 | (C23) |
| A1.3 | B1.11 | (C24) |
| A1.3 | B1.11 | (C25) |
| A1.3 | B1.11 | (C28) |
| A1.3 | B1.11 | (C32) |
| A1.3 | B1.11 | (C37) |
| A1.3 | B1.11 | (C40) |
| A1.3 | B1.11 | (C41) |
| A1.3 | B1.11 | (C42) |
| A1.3 | B1.11 | (C43) |
| A1.3 | B1.11 | (C51) |
| A1.3 | B1.11 | (C52) |
| A1.3 | B1.11 | (C57) |
| A1.3 | B1.11 | (C58) |
| A1.3 | B1.11 | (C59) |
| A1.3 | B1.11 | (C60) |
| A1.3 | B1.11 | (C61) |
| A1.3 | B1.11 | (C62) |
| A1.3 | B1.11 | (C65) |
| A1.3 | B1.11 | (C66) |
| A1.3 | B1.11 | (C71) |
| A1.3 | B1.11 | (C74) |
| A1.3 | B1.12 | (C1) |
| A1.3 | B1.12 | (C2) |
| A1.3 | B1.12 | (C3) |
| A1.3 | B1.12 | (C4) |
| A1.3 | B1.12 | (C5) |
| A1.3 | B1.12 | (C7) |
| A1.3 | B1.12 | (C9) |
| A1.3 | B1.12 | (C12) |
| A1.3 | B1.12 | (C13) |
| A1.3 | B1.12 | (C15) |
| A1.3 | B1.12 | (C18) |
| A1.3 | B1.12 | (C21) |

TABLE 2-continued

| Active compound (A) | Active compound (B) | Active compound (C) |
|---|---|---|
| A1.3 | B1.12 | (C22) |
| A1.3 | B1.12 | (C23) |
| A1.3 | B1.12 | (C24) |
| A1.3 | B1.12 | (C25) |
| A1.3 | B1.12 | (C28) |
| A1.3 | B1.12 | (C32) |
| A1.3 | B1.12 | (C37) |
| A1.3 | B1.12 | (C40) |
| A1.3 | B1.12 | (C41) |
| A1.3 | B1.12 | (C42) |
| A1.3 | B1.12 | (C43) |
| A1.3 | B1.12 | (C51) |
| A1.3 | B1.12 | (C52) |
| A1.3 | B1.12 | (C57) |
| A1.3 | B1.12 | (C58) |
| A1.3 | B1.12 | (C59) |
| A1.3 | B1.12 | (C60) |
| A1.3 | B1.12 | (C61) |
| A1.3 | B1.12 | (C62) |
| A1.3 | B1.12 | (C65) |
| A1.3 | B1.12 | (C66) |
| A1.3 | B1.12 | (C71) |
| A1.3 | B1.12 | (C74) |
| A1.3 | B1.13 | (C1) |
| A1.3 | B1.13 | (C2) |
| A1.3 | B1.13 | (C3) |
| A1.3 | B1.13 | (C4) |
| A1.3 | B1.13 | (C5) |
| A1.3 | B1.13 | (C7) |
| A1.3 | B1.13 | (C9) |
| A1.3 | B1.13 | (C12) |
| A1.3 | B1.13 | (C13) |
| A1.3 | B1.13 | (C15) |
| A1.3 | B1.13 | (C18) |
| A1.3 | B1.13 | (C21) |
| A1.3 | B1.13 | (C22) |
| A1.3 | B1.13 | (C23) |
| A1.3 | B1.13 | (C24) |
| A1.3 | B1.13 | (C25) |
| A1.3 | B1.13 | (C28) |
| A1.3 | B1.13 | (C32) |
| A1.3 | B1.13 | (C37) |
| A1.3 | B1.13 | (C40) |
| A1.3 | B1.13 | (C41) |
| A1.3 | B1.13 | (C42) |
| A1.3 | B1.13 | (C43) |
| A1.3 | B1.13 | (C51) |
| A1.3 | B1.13 | (C52) |
| A1.3 | B1.13 | (C57) |
| A1.3 | B1.13 | (C58) |
| A1.3 | B1.13 | (C59) |
| A1.3 | B1.13 | (C60) |
| A1.3 | B1.13 | (C61) |
| A1.3 | B1.13 | (C62) |
| A1.3 | B1.13 | (C62) |
| A1.3 | B1.13 | (C65) |
| A1.3 | B1.13 | (C66) |
| A1.3 | B1.13 | (C71) |
| A1.3 | B1.13 | (C74) |
| A1.3 | B1.14 | (C1) |
| A1.3 | B1.14 | (C2) |
| A1.3 | B1.14 | (C3) |
| A1.3 | B1.14 | (C4) |
| A1.3 | B1.14 | (C5) |
| A1.3 | B1.14 | (C7) |
| A1.3 | B1.14 | (C9) |
| A1.3 | B1.14 | (C12) |
| A1.3 | B1.14 | (C13) |
| A1.3 | B1.14 | (C15) |
| A1.3 | B1.14 | (C18) |
| A1.3 | B1.14 | (C21) |
| A1.3 | B1.14 | (C22) |
| A1.3 | B1.14 | (C23) |
| A1.3 | B1.14 | (C24) |
| A1.3 | B1.14 | (C25) |
| A1.3 | B1.14 | (C28) |
| A1.3 | B1.14 | (C32) |
| A1.3 | B1.14 | (C37) |
| A1.3 | B1.14 | (C37) |
| A1.3 | B1.14 | (C40) |
| A1.3 | B1.14 | (C41) |
| A1.3 | B1.14 | (C42) |
| A1.3 | B1.14 | (C43) |
| A1.3 | B1.14 | (C51) |
| A1.3 | B1.14 | (C52) |
| A1.3 | B1.14 | (C57) |
| A1.3 | B1.14 | (C58) |
| A1.3 | B1.14 | (C59) |
| A1.3 | B1.14 | (C60) |
| A1.3 | B1.14 | (C61) |
| A1.3 | B1.14 | (C62) |
| A1.3 | B1.14 | (C65) |
| A1.3 | B1.14 | (C66) |
| A1.3 | B1.14 | (C71) |
| A1.3 | B1.14 | (C74) |
| A1.3 | B1.15 | (C1) |
| A1.3 | B1.15 | (C2) |
| A1.3 | B1.15 | (C3) |
| A1.3 | B1.15 | (C4) |
| A1.3 | B1.15 | (C5) |
| A1.3 | B1.15 | (C7) |
| A1.3 | B1.15 | (C9) |
| A1.3 | B1.15 | (C12) |
| A1.3 | B1.15 | (C13) |
| A1.3 | B1.15 | (C15) |
| A1.3 | B1.15 | (C18) |
| A1.3 | B1.15 | (C21) |
| A1.3 | B1.15 | (C22) |
| A1.3 | B1.15 | (C23) |
| A1.3 | B1.15 | (C24) |
| A1.3 | B1.15 | (C25) |
| A1.3 | B1.15 | (C28) |
| A1.3 | B1.15 | (C32) |
| A1.3 | B1.15 | (C37) |
| A1.3 | B1.15 | (C40) |
| A1.3 | B1.15 | (C41) |
| A1.3 | B1.15 | (C42) |
| A1.3 | B1.15 | (C43) |
| A1.3 | B1.15 | (C51) |
| A1.3 | B1.15 | (C52) |
| A1.3 | B1.15 | (C57) |
| A1.3 | B1.15 | (C58) |
| A1.3 | B1.15 | (C59) |
| A1.3 | B1.15 | (C60) |
| A1.3 | B1.15 | (C61) |
| A1.3 | B1.15 | (C62) |
| A1.3 | B1.15 | (C65) |
| A1.3 | B1.15 | (C66) |
| A1.3 | B1.15 | (C71) |
| A1.3 | B1.15 | (C74) |
| A1.3 | B1.16 | (C1) |
| A1.3 | B1.16 | (C2) |
| A1.3 | B1.16 | (C3) |
| A1.3 | B1.16 | (C4) |
| A1.3 | B1.16 | (C5) |
| A1.3 | B1.16 | (C7) |
| A1.3 | B1.16 | (C9) |
| A1.3 | B1.16 | (C12) |
| A1.3 | B1.16 | (C13) |
| A1.3 | B1.16 | (C15) |
| A1.3 | B1.16 | (C18) |
| A1.3 | B1.16 | (C21) |
| A1.3 | B1.16 | (C22) |
| A1.3 | B1.16 | (C23) |
| A1.3 | B1.16 | (C24) |
| A1.3 | B1.16 | (C25) |
| A1.3 | B1.16 | (C28) |
| A1.3 | B1.16 | (C32) |
| A1.3 | B1.16 | (C37) |
| A1.3 | B1.16 | (C37) |
| A1.3 | B1.16 | (C40) |
| A1.3 | B1.16 | (C41) |

TABLE 2-continued

| Active compound (A) | Active compound (B) | Active compound (C) |
|---|---|---|
| A1.3 | B1.16 | (C42) |
| A1.3 | B1.16 | (C43) |
| A1.3 | B1.16 | (C51) |
| A1.3 | B1.16 | (C52) |
| A1.3 | B1.16 | (C57) |
| A1.3 | B1.16 | (C58) |
| A1.3 | B1.16 | (C59) |
| A1.3 | B1.16 | (C60) |
| A1.3 | B1.16 | (C61) |
| A1.3 | B1.16 | (C62) |
| A1.3 | B1.16 | (C65) |
| A1.3 | B1.16 | (C66) |
| A1.3 | B1.16 | (C71) |
| A1.3 | B1.16 | (C74) |
| A1.3 | B1.17 | (C1) |
| A1.3 | B1.17 | (C2) |
| A1.3 | B1.17 | (C3) |
| A1.3 | B1.17 | (C4) |
| A1.3 | B1.17 | (C5) |
| A1.3 | B1.17 | (C7) |
| A1.3 | B1.17 | (C9) |
| A1.3 | B1.17 | (C12) |
| A1.3 | B1.17 | (C13) |
| A1.3 | B1.17 | (C15) |
| A1.3 | B1.17 | (C18) |
| A1.3 | B1.17 | (C21) |
| A1.3 | B1.17 | (C22) |
| A1.3 | B1.17 | (C23) |
| A1.3 | B1.17 | (C24) |
| A1.3 | B1.17 | (C25) |
| A1.3 | B1.17 | (C28) |
| A1.3 | B1.17 | (C32) |
| A1.3 | B1.17 | (C37) |
| A1.3 | B1.17 | (C40) |
| A1.3 | B1.17 | (C41) |
| A1.3 | B1.17 | (C42) |
| A1.3 | B1.17 | (C43) |
| A1.3 | B1.17 | (C51) |
| A1.3 | B1.17 | (C52) |
| A1.3 | B1.17 | (C57) |
| A1.3 | B1.17 | (C58) |
| A1.3 | B1.17 | (C59) |
| A1.3 | B1.17 | (C60) |
| A1.3 | B1.17 | (C61) |
| A1.3 | B1.17 | (C62) |
| A1.3 | B1.17 | (C65) |
| A1.3 | B1.17 | (C66) |
| A1.3 | B1.17 | (C71) |
| A1.3 | B1.17 | (C74) |
| A1.3 | B1.18 | (C1) |
| A1.3 | B1.18 | (C2) |
| A1.3 | B1.18 | (C3) |
| A1.3 | B1.18 | (C4) |
| A1.3 | B1.18 | (C5) |
| A1.3 | B1.18 | (C7) |
| A1.3 | B1.18 | (C9) |
| A1.3 | B1.18 | (C12) |
| A1.3 | B1.18 | (C13) |
| A1.3 | B1.18 | (C15) |
| A1.3 | B1.18 | (C18) |
| A1.3 | B1.18 | (C21) |
| A1.3 | B1.18 | (C22) |
| A1.3 | B1.18 | (C23) |
| A1.3 | B1.18 | (C24) |
| A1.3 | B1.18 | (C25) |
| A1.3 | B1.18 | (C28) |
| A1.3 | B1.18 | (C32) |
| A1.3 | B1.18 | (C37) |
| A1.3 | B1.18 | (C40) |
| A1.3 | B1.18 | (C41) |
| A1.3 | B1.18 | (C42) |
| A1.3 | B1.18 | (C51) |
| A1.3 | B1.18 | (C52) |
| A1.3 | B1.18 | (C57) |
| A1.3 | B1.18 | (C58) |
| A1.3 | B1.18 | (C59) |
| A1.3 | B1.18 | (C60) |
| A1.3 | B1.18 | (C61) |
| A1.3 | B1.18 | (C62) |
| A1.3 | B1.18 | (C65) |
| A1.3 | B1.18 | (C66) |
| A1.3 | B1.18 | (C71) |
| A1.3 | B1.18 | (C74) |
| A1.3 | B1.19 | (C1) |
| A1.3 | B1.19 | (C2) |
| A1.3 | B1.19 | (C3) |
| A1.3 | B1.19 | (C4) |
| A1.3 | B1.19 | (C5) |
| A1.3 | B1.19 | (C7) |
| A1.3 | B1.19 | (C9) |
| A1.3 | B1.19 | (C12) |
| A1.3 | B1.19 | (C13) |
| A1.3 | B1.19 | (C15) |
| A1.3 | B1.19 | (C18) |
| A1.3 | B1.19 | (C21) |
| A1.3 | B1.19 | (C22) |
| A1.3 | B1.19 | (C23) |
| A1.3 | B1.19 | (C24) |
| A1.3 | B1.19 | (C25) |
| A1.3 | B1.19 | (C28) |
| A1.3 | B1.19 | (C32) |
| A1.3 | B1.19 | (C37) |
| A1.3 | B1.19 | (C40) |
| A1.3 | B1.19 | (C41) |
| A1.3 | B1.19 | (C42) |
| A1.3 | B1.19 | (C43) |
| A1.3 | B1.19 | (C51) |
| A1.3 | B1.19 | (C52) |
| A1.3 | B1.19 | (C57) |
| A1.3 | B1.19 | (C58) |
| A1.3 | B1.19 | (C59) |
| A1.3 | B1.19 | (C60) |
| A1.3 | B1.19 | (C61) |
| A1.3 | B1.19 | (C62) |
| A1.3 | B1.19 | (C65) |
| A1.3 | B1.19 | (C66) |
| A1.3 | B1.19 | (C71) |
| A1.3 | B1.19 | (C74) |
| A1.3 | B1.20 | (C1) |
| A1.3 | B1.20 | (C2) |
| A1.3 | B1.20 | (C3) |
| A1.3 | B1.20 | (C4) |
| A1.3 | B1.20 | (C5) |
| A1.3 | B1.20 | (C7) |
| A1.3 | B1.20 | (C9) |
| A1.3 | B1.20 | (C12) |
| A1.3 | B1.20 | (C13) |
| A1.3 | B1.20 | (C15) |
| A1.3 | B1.20 | (C18) |
| A1.3 | B1.20 | (C21) |
| A1.3 | B1.20 | (C22) |
| A1.3 | B1.20 | (C23) |
| A1.3 | B1.20 | (C24) |
| A1.3 | B1.20 | (C25) |
| A1.3 | B1.20 | (C28) |
| A1.3 | B1.20 | (C32) |
| A1.3 | B1.20 | (C37) |
| A1.3 | B1.20 | (C40) |
| A1.3 | B1.20 | (C41) |
| A1.3 | B1.20 | (C42) |
| A1.3 | B1.20 | (C43) |
| A1.3 | B1.20 | (C51) |
| A1.3 | B1.20 | (C52) |
| A1.3 | B1.20 | (C57) |
| A1.3 | B1.20 | (C58) |
| A1.3 | B1.20 | (C59) |
| A1.3 | B1.20 | (C60) |
| A1.3 | B1.20 | (C61) |
| A1.3 | B1.20 | (C62) |
| A1.3 | B1.20 | (C65) |
| A1.3 | B1.20 | (C66) |
| A1.3 | B1.20 | (C71) |

TABLE 2-continued

| Active compound (A) | Active compound (B) | Active compound (C) |
|---|---|---|
| A1.3 | B1.20 | (C74) |
| A1.3 | B1.21 | (C1) |
| A1.3 | B1.21 | (C2) |
| A1.3 | B1.21 | (C3) |
| A1.3 | B1.21 | (C4) |
| A1.3 | B1.21 | (C5) |
| A1.3 | B1.21 | (C7) |
| A1.3 | B1.21 | (C9) |
| A1.3 | B1.21 | (C12) |
| A1.3 | B1.21 | (C13) |
| A1.3 | B1.21 | (C15) |
| A1.3 | B1.21 | (C18) |
| A1.3 | B1.21 | (C21) |
| A1.3 | B1.21 | (C22) |
| A1.3 | B1.21 | (C23) |
| A1.3 | B1.21 | (C24) |
| A1.3 | B1.21 | (C25) |
| A1.3 | B1.21 | (C28) |
| A1.3 | B1.21 | (C32) |
| A1.3 | B1.21 | (C37) |
| A1.3 | B1.21 | (C40) |
| A1.3 | B1.21 | (C41) |
| A1.3 | B1.21 | (C42) |
| A1.3 | B1.21 | (C43) |
| A1.3 | B1.21 | (C51) |
| A1.3 | B1.21 | (C52) |
| A1.3 | B1.21 | (C57) |
| A1.3 | B1.21 | (C58) |
| A1.3 | B1.21 | (C59) |
| A1.3 | B1.21 | (C60) |
| A1.3 | B1.21 | (C61) |
| A1.3 | B1.21 | (C62) |
| A1.3 | B1.21 | (C65) |
| A1.3 | B1.21 | (C66) |
| A1.3 | B1.21 | (C71) |
| A1.3 | B1.21 | (C74) |
| A1.3 | B1.22 | (C1) |
| A1.3 | B1.22 | (C2) |
| A1.3 | B1.22 | (C3) |
| A1.3 | B1.22 | (C4) |
| A1.3 | B1.22 | (C5) |
| A1.3 | B1.22 | (C7) |
| A1.3 | B1.22 | (C9) |
| A1.3 | B1.22 | (C12) |
| A1.3 | B1.22 | (C13) |
| A1.3 | B1.22 | (C15) |
| A1.3 | B1.22 | (C18) |
| A1.3 | B1.22 | (C21) |
| A1.3 | B1.22 | (C22) |
| A1.3 | B1.22 | (C23) |
| A1.3 | B1.22 | (C24) |
| A1.3 | B1.22 | (C25) |
| A1.3 | B1.22 | (C28) |
| A1.3 | B1.22 | (C32) |
| A1.3 | B1.22 | (C37) |
| A1.3 | B1.22 | (C40) |
| A1.3 | B1.22 | (C41) |
| A1.3 | B1.22 | (C42) |
| A1.3 | B1.22 | (C43) |
| A1.3 | B1.22 | (C51) |
| A1.3 | B1.22 | (C52) |
| A1.3 | B1.22 | (C57) |
| A1.3 | B1.22 | (C58) |
| A1.3 | B1.22 | (C59) |
| A1.3 | B1.22 | (C60) |
| A1.3 | B1.22 | (C61) |
| A1.3 | B1.22 | (C62) |
| A1.3 | B1.22 | (C62) |
| A1.3 | B1.22 | (C65) |
| A1.3 | B1.22 | (C66) |
| A1.3 | B1.22 | (C71) |
| A1.3 | B1.22 | (C74) |
| A1.3 | B1.23 | (C1) |
| A1.3 | B1.23 | (C2) |
| A1.3 | B1.23 | (C3) |
| A1.3 | B1.23 | (C4) |
| A1.3 | B1.23 | (C5) |
| A1.3 | B1.23 | (C7) |
| A1.3 | B1.23 | (C9) |
| A1.3 | B1.23 | (C12) |
| A1.3 | B1.23 | (C13) |
| A1.3 | B1.23 | (C15) |
| A1.3 | B1.23 | (C18) |
| A1.3 | B1.23 | (C21) |
| A1.3 | B1.23 | (C22) |
| A1.3 | B1.23 | (C23) |
| A1.3 | B1.23 | (C24) |
| A1.3 | B1.23 | (C25) |
| A1.3 | B1.23 | (C28) |
| A1.3 | B1.23 | (C32) |
| A1.3 | B1.23 | (C37) |
| A1.3 | B1.23 | (C40) |
| A1.3 | B1.23 | (C41) |
| A1.3 | B1.23 | (C42) |
| A1.3 | B1.23 | (C43) |
| A1.3 | B1.23 | (C51) |
| A1.3 | B1.23 | (C52) |
| A1.3 | B1.23 | (C57) |
| A1.3 | B1.23 | (C58) |
| A1.3 | B1.23 | (C59) |
| A1.3 | B1.23 | (C60) |
| A1.3 | B1.23 | (C61) |
| A1.3 | B1.23 | (C62) |
| A1.3 | B1.23 | (C65) |
| A1.3 | B1.23 | (C66) |
| A1.3 | B1.23 | (C71) |
| A1.3 | B1.23 | (C74) |

The application rates of the active compounds (C) may vary strongly. The following ranges may serve as a rough guide for herbicidally active compounds (C):
in general 0.5-5000 g AS/ha, preferably 1 to 3000 g AS/ha, particularly preferably 2-2000 g AS/ha.

If the active compound (C) used is a safener, this is preferably employed in a weight ratio of from 1:10 to 10:1 relative to the active compound (B).

Some of the combinations mentioned are novel and as such also part of the subject of the invention.

The combinations according to the invention (=herbicidal compositions) have an outstanding herbicidal activity against a broad spectrum of economically important monocotyledonous and dicotyledonous harmful plants. The active compounds also act efficiently on perennial weeds which produce shoots from rhizomes, rootstocks or other perennial organs and which are difficult to control. In this context, it does not matter whether the compounds are applied before sowing, pre-emergence or post-emergence. Post-emergence application, or early post-sowing pre-emergence application, is preferred.

Specifically, examples may be mentioned of some representatives of the monocotyledonous and dicotyledonous weed flora which can be controlled by the compositions according to the invention, without the enumeration being a restriction to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous harmful plants of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth likewise stops drastically a very short time after the treatment (with growth deformations, chloroses and necroses) and the weed plants remain at the growth stage of the point of time of application, or they die completely after a certain time, so that in this manner competition by the weeds, which is harmful to the crop plants, is eliminated at a very early point in time and in a sustained manner.

In comparison with the individual preparations, the herbicidal compositions according to the invention are distinguished by a more rapidly commencing and longer lasting herbicidal action. As a rule, the rainfastness of the active compounds in the combinations according to the invention is advantageous. A particular advantage is that the dosages of the compounds (A) and (B), which are used in the combinations and are effective, can be adjusted to such a low quantity that their soil action is optimal. This does not only allow them to be employed in sensitive crops in the first place, but groundwater contaminations are virtually avoided. The active-compound-combination according to the invention allows the application rate of the active compounds required to be reduced considerably.

When herbicides of the type (A)+(B) are used jointly, superadditive (=synergistic) effects are observed. This means that the effect in the combinations exceeds the expected total of the effects of the individual herbicides employed. The synergistic effects allow the application rate to be reduced, a broader spectrum of broad-leaved weeds and weed grasses to be controlled, the herbicidal effect to take place more rapidly, the duration of action to be longer, the harmful plants to be controlled better while using only one, or few, applications, and the application period which is possible to be extended. In some cases, uptake of the compositions also reduces the amount of harmful constituents in the crop plant, such as nitrogen or oleic acid.

The abovementioned properties and advantages are necessary under practical weed control conditions to keep agricultural crops free from undesired competing plants and thus to guarantee and/or increase the yields from the qualitative and quantitative point of view. These novel combinations markedly exceed the technical state of the art with a view to the properties described.

While the compounds according to the invention have an outstanding herbicidal activity against monocotyledonous and dicotyledonous weeds, the tolerant, or cross-tolerant, cereal plants are damaged only to a minor extent, or not at all.

Moreover, some of the compositions according to the invention have outstanding growth-regulatory properties on the cereal plants. They engage in the plants' metabolism in a regulatory manner and can thus be employed for provoking directed effects on plant constituents. Moreover, they are also suitable for the general control and inhibition of undesired vegetative growth without simultaneously destroying the plants. An inhibition of vegetative growth is very important in a large number of monocotyledonous and dicotyledonous crops since lodging can thus be reduced, or prevented completely.

Owing to their herbicidal and plant-growth-regulatory properties, the compositions can be employed for controlling harmful plants in known tolerant or cross-tolerant cereal crops, or in tolerant or genetically engineered cereal crops still to be developed. As a rule, the transgenic plants are distinguished by particular, advantageous properties, in addition to resistances to the compositions according to the invention, for example, by resistances to plant diseases or pathogens of plant diseases such as particular insects or microorganisms such as fungi, bacteria or viruses. Other particular properties relate, for example, to the harvested material with regard to quantity, quality, storability, composition and specific constituents. Thus, transgenic plants are known whose oil content is increased or whose quality is altered, for example where the harvested material has a different fatty acid composition.

Conventional methods of generating novel plants which have modified properties in comparison to plants occurring to date consist, for example, in traditional breeding methods and the generation of mutants. Alternatively, novel plants with altered properties can be generated with the aid of genetic engineering methods (see, for example, EP-A-0221044, EP-A-0131624). For example, the following were described in several cases:

genetic modifications of crop plants for the purpose of modifying the starch synthesized in the plants (for example WO 92/011376 A, WO 92/014827 A, WO 91/019806 A), transgenic crop plants which are resistant to certain herbicides of the glyphosate type (WO 92/000377 A) or of the sulfonylurea type (EP 0 257 993 A, U.S. Pat. No. 5,013, 659) or to combinations or mixtures of these herbicides through "gene stacking", such as transgenic crop plants e.g. corn or soybean with the tradename or the name Optimum™ GAT™ (glyphosate ALS tolerant).

transgenic crop plants, for example cotton, with the capability of producing *Bacillus thuringiensis* toxins (Bt toxins) which make the plants resistant to certain pests (EP-A 0 142 924 A, EP-A 0 193 259 A).

transgenic crop plants having a modified fatty acid composition (WO 91/013972 A).

genetically modified crop plants having novel constituents or secondary compounds, for example novel phytoalexins providing increased resistance to disease (EP 0 309 862 A, EP 0464 461 A)

genetically modified plants having reduced photorespiration, which provide higher yields and have higher stress tolerance (EP 0 305 398 A)

transgenic crop plants producing pharmaceutically or diagnostically important proteins ("molecular pharming")

transgenic crop plants distinguished by higher yields or better quality transgenic crop plants distinguished by a combination, for example of the novel properties mentioned above ("gene stacking")

A large number of molecular-biological techniques with which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg; or Christou, "Trends in Plant Science" 1 (1996) 423-431).

To carry out such recombinant manipulations, nucleic acid molecules can be introduced into plasmids which permit a mutagenesis or a sequence modification by recombination of DNA sequences. For example, it is possible with the aid of standard methods to carry out base exchanges, to remove sub-sequences or to add natural or synthetic sequences. Adapters or linkers may be added in order to link the DNA fragments to each other, see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment.

Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). Expression of the nucleic acid molecules may also take place in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

Preferably, the compositions according to the invention can be employed in transgenic cereal crops which are not only tolerant to component (A), but also to herbicides which inhibit essential plant enzymes, for example acetolactate synthases (ALS), EPSP synthases or hydroxyphenylpyruvate dioxygenases (HPPD), or to herbicides from the group of the sulfonylureas, glyphosates or benzoylisoxazoles and analogous active compounds or to any combinations of these active compounds.

Particularly preferably, the herbicidal compositions according to the invention can be used in transgenic crop plants which are tolerant to a combination of glyphosates and glufosinates or to a combination of glufosinates and sulfonylureas or imidazolinones.

Accordingly, the invention also provides a method for controlling unwanted vegetation in tolerant cereal crops wherein one or more herbicides of type (A) are applied with one or more herbicides of type (B) to the harmful plants, plant parts thereof or the area under cultivation.

The invention also provides the novel combinations of compounds (A)+(B) and the herbicidal compositions comprising them.

The active compound combinations according to the invention can be present either as mixed formulations of the two components, optionally with further active compounds, additives and/or customary formulation auxiliaries, which are then applied in a customary manner diluted with water, or as tankmixes by joint dilution of the separately formulated or partially separately formulated components with water.

The compounds according to the invention can be employed in the form of wettable powders, emulsifiable concentrates, sprayable solutions, dusts or granules in the customary preparations. The invention therefore furthermore provides herbicidal and plant-growth regulating compositions comprising compositions according to the invention.

The compositions according to the invention can be formulated in various ways, depending on the prevailing biological and/or physicochemical parameters. The following are examples of possible formulations: wettable powders (WP), water-soluble powders (SP), water-soluble concentrates, emulsifiable concentrates (EC), emulsions (EW), such as oil-in-water and water-in-oil emulsionen, sprayable solutions, suspension concentrates (SC), oil- or water-based dispersions, oil-miscible solutions, capsule suspensions (CS), dusts (DP), seed-dressing materials, granules for broadcasting and for soil application, granules (GR) in the form of microgranules, spray granules, coated granules and adsorption granules, water-dispersible granules (WG), water-soluble granules (SG), ULV formulations, microcapsules and waxes.

The individual formulation types are known in principle and are described, for example, in: Winnacker-Küchler, "Chemische Technologie" [Chemical Engineering], Volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd ed., Darland Books, Caldwell N.J.; H. v. Olphen, "Introduction to Clay Colloid Chemistry"; 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschafts, Stuttgart 1976, Winnacker-Küchler, "Chemische Technologie", Volume 7, C. Hanser Verlag Munich, 4th ed. 1986.

Based on these formulations, it is also possible to prepare combinations with other pesticidally active compounds such as insecticides, acaricides, herbicides, fungicides and also with safeners, fertilizers and/or growth regulators, for example in the form of a readymix or as tank mix.

Wettable powders are products which are uniformly dispersible in water and which, besides the active compounds and in addition to one or more diluents or inert substances, also comprise ionic and/or nonionic surfactants (wetting agents, dispersants), for example polyoxyethylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltauride. To prepare the wettable powders, the herbicidally active compounds are finely ground, for example in customary apparatuses such as hammer mills, blower mills and airjet mills and simultaneously or subsequently mixed with the formulation auxiliaries.

Emulsifiable concentrates are prepared by dissolving the active compound in an organic solvent or solvent mixture, for example butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which may be used are: calcium salts of alkylarylsulfonic acids, such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide copolymers, alkyl polyethers, sorbitan esters such as sorbitan fatty acid esters, or polyoxyethylene sorbitan esters such as polyoxyethylene sorbitan fatty acid esters.

Dusts are obtained by grinding the active compound with finely divided solid materials, for example talc, natural clays such as kaolin, bentonite and pyrophyllite, or diatomaceous earth.

Suspension concentrates can be water-based or oil-based. They can be prepared, for example, by wet grinding by means of commercially available bead mills and, if appropriate, addition of surfactants as they have already been mentioned for example above for the other formulation types.

Emulsions, for example oil-in-water emulsions (EW), can be prepared, for example, by means of stirrers, colloid mills and/or static mixers using aqueous organic solvents and, if appropriate, surfactants as have already been mentioned for example for the other formulation types.

Granules can be prepared either by spraying the active compound onto adsorptive, granulated inert material or by applying active compound concentrates to the surface of carriers such as sand, kaolites or granulated inert material with the aid of binders, for example polyvinyl alcohol, sodium polyacrylate or else mineral oils. Suitable active compounds may also be granulated in the manner conventionally used for the production of fertilizer granules, if desired in a mixture with fertilizers.

Water-dispersible granules are generally prepared by processes such as spray drying, fluidized-bed granulation, disk granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of compounds according to the invention.

In wettable powders, the active compound concentration is, for example, from about 10 to 90% by weight; the remainder to 100% by weight consists of customary formulation constituents. In the case of emulsifiable concentrates, the active compound concentration may be from about 1 to 90% by weight, preferably from 5 to 80% by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In water-dispersible granules, the active compound content depends partly on whether the active compound is present in solid or liquid form and which granulation assistants, fillers, etc. are used. In the granules dispersible in water, the content of active compound is, for example, between 1 and 95% by weight, preferably between 10 and 80% by weight.

In addition, the abovementioned active compound formulations may comprise, if appropriate, the conventional adhesives, wetters, dispersants, emulsifiers, preservatives, antifreeze agents, solvents, fillers, colors, carriers, antifoams, evaporation inhibitors, pH regulators or viscosity regulators.

For example, it is known that the effect of glufosinate-ammonium (A1.2) and of its L-enantiomer can be improved by surfactants, preferably by wetters from the series of the alkyl polyglycol ether sulfates which contain, for example, 10 to 18 carbon atoms and which are used in the form of their alkali metal salts or ammonium salts, but also as the magnesium salt, such as sodium $C_{12}/C_{14}$-fatty alcohol diglycol ether sulfate (®Genapol LRO, Hoechst); see EP-A-0476555, EP-A-0048436, EP-A-0336151 or U.S. Pat. No. 4,400,196 and Proc. EWRS Symp. "Factors Affecting Herbicidal Activity and Selectivity", 227-232 (1988). Moreover, it is known that alkyl polyglycol ether sulfates are also suitable as penetrants and synergists for a series of other herbicides, inter alia also herbicides from the series of the imidazolinones; see EP-A-0502014.

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further prior to use with other inert compounds.

The active compounds can be applied to the plants, parts of the plants, seeds of the plants or the area under cultivation (soil of a field), preferably to the green plants and parts of the plants and, if appropriate, additionally to the soil of the field.

One possible use is the joint application of the active compounds in the form of tank mixes, the concentrated formulations of the individual active compounds, in optimal formulations, jointly being mixed with water in the tank and the resulting spray mixture being applied.

A joint herbicidal formulation of the combination according to the invention of the active compounds (A) and (B) has the advantage of being easier to apply since the quantities of the components are already presented in the correct ratio to each other. Moreover, the adjuvants in the formulation can be matched optimally to each other, while a tank mix of different formulations may lead to undesired combinations of adjuvants.

A. Formulation examples a) A dust is obtained by mixing 10 parts by weight of an active compound combination according to the invention and 90 parts by weight of talc as inert material and comminuting the mixture in a hammer mill.

b) A wettable powder which is readily dispersible in water is obtained by mixing 25 parts by weight of an active compound combination according to the invention, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of an active compound combination according to the invention with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to 277 C), and grinding the mixture in a ball mill to a fineness of below 5 microns.

d) An emulsifiable concentrate is obtained from 15 parts by weight of an active compound combination according to the invention, 75 parts by weight of cyclohexanone as solvent and 10 parts by weight of oxethylated nonylphenol as emulsifier.

e) Water-dispersible granules are obtained by mixing
    75 parts by weight of an active compound combination according to the invention,
    10 parts by weight of calcium lignosulfonate,
    5 parts by weight of sodium lauryl sulfate,
    3 parts by weight of polyvinyl alcohol and
    7 parts by weight of kaolin,
    grinding the mixture on a pinned-disk mill and granulating the powder in a fluidized bed by spraying on water as granulation liquid.

f) Water-dispersible granules are also obtained by homogenizing and precomminuting, on a colloid mill,
    25 parts by weight of an active compound combination according to the invention,
    5 parts by weight of sodium 2,2'-dinaphthylmethane-6,6'-disulfonate,
    2 parts by weight of sodium oleoylmethyltaurinate,
    1 part by weight of polyvinyl alcohol,
    17 parts by weight of calcium carbonate and
    50 parts by weight of water,
    subsequently grinding the mixture in a bead mill and atomizing and drying the resulting suspension in a spray tower by means of a single-substance nozzle.

B. Biological examples

1. Pre-Emergence Effect on Weeds

Seeds or rhizome pieces of monocotyledonous and dicotyledonous weed plants are placed in sandy loam soil in plastic or cardboard pots and covered with soil. The compositions which are formulated in the form of concentrated aqueous solutions, wettable powders or emulsion concentrates are then applied to the surface of the soil cover in the form of an aqueous solution, suspension or emulsion at an application rate of 100 to 800 l of water/ha (converted), in various dosages. After the treatment, the pots are placed in a greenhouse and kept under good growth conditions for the weeds. After the test plants have emerged, the damage to the plants or the emergence damage is scored visually after a test period of 3 to 4 weeks by comparison with untreated controls. As shown by the test results, the compositions according to the invention have a good herbicidal pre-emergence activity against a broad spectrum of weed grasses and broad-leaved weeds.

Frequently, effects of the combinations according to the invention are observed which exceed the formal total of the effects when applying the herbicides individually (=synergistic effect).

If the data of the effects observed (=E) already exceed the formal total (=$E^A$=A+B) of the data of the experiments with individual applications, then they also exceed Colby's expected value (=$E^C$), which is calculated using the formula which follows and which is also considered to be suggestive of synergism (cf. S. R. Colby; in Weeds 15 (1967) pp. 20 to 22):

$$E^C = A + B - (A \cdot B / 100)$$

Here: A, B=effect of the active compounds A and B, respectively, in % at a and b g, respectively, of AS/ha; $E^C$=expected value in % at a+b g of AS/ha.

At suitably low dosages, the observed values of the experiments show an effect of the combinations which exceeds the expected values according to Colby.

2. Post-Emergence Effect on Weeds

Seeds or rhizome pieces of monocotyledonous and dicotyledonous weeds are placed in sandy loam soil in cardboard pots, covered with soil and grown in the greenhouse under good growth conditions. Three weeks after sowing, the test plants at the two- to four-leaf stage are treated with the compositions according to the invention. The compositions according to the invention which are formulated as wettable powders or as emulsion concentrates are sprayed in various dosages on the green parts of the plants at an application rate of 100 to 800 l of water/ha (converted). After the test plants have remained in the greenhouse for about 3 to 4 weeks under optimal growth conditions, the effect of the products is scored visually by comparison with untreated controls. On post-emergence application, too, the compositions according to the invention have a good herbicidal activity against a broad spectrum of economically important weed grasses and broad-leaved weeds.

Frequently, effects of the combinations according to the invention are observed which exceed the formal total of the effects when applying the herbicides individually. At suitably low dosages, the observed data of the experiments show an effect of the combinations which exceeds the expected values according to Colby (cf. scoring in Example 1).

3. Herbicidal Effect and Crop Plant Compatibility (Field Trial)

Transgenic cereal plants resistant to one or more herbicides (A) are grown together with typical weed plants in the open on 2×5 m plots under natural field conditions; in addition, weed infestation occurs naturally during cultivation of the cereal plants. The treatment with the compositions according to the invention and, as control, separately by only applying the active compounds of the components, was carried out under standard conditions with a plot sprayer at an application rate of 100-400 liters of water per hectare in parallel tests as can be seen from the scheme in Table 1, i.e. pre-sowing pre-emergence, post-sowing pre-emergence or post-emergence in the early, medium or late stage.

TABLE 3

Use scheme - examples

| Application of the active compounds | Pre-sowing | Pre-emergence post-sowing | Post-emergence 1-2-leaf | Post-emergence 2-4-leaf | Post-emergence 6-leaf |
|---|---|---|---|---|---|
| combined | (A) + (B) | | | | |
| " | | (A) + (B) | | | |
| " | | | (A) + (B) | | |
| " | | | | (A) + (B) | |
| " | | | | | (A) + (B) |

TABLE 3-continued

Use scheme - examples

| Application of the active compounds | Pre-sowing | Pre-emergence post-sowing | Post-emergence 1-2-leaf | Post-emergence 2-4-leaf | Post-emergence 6-leaf |
|---|---|---|---|---|---|
| sequential | (A) |  | (B) |  |  |
| " |  | (A) | (B) |  |  |
| " |  | (A) |  | (B) |  |
| " |  | (A) | (A) | (B) |  |
| " |  | (A) |  | (B) | (B) |
| " |  | (A) |  | (A) + (B) |  |
| " | (B) |  | (A) |  |  |
| " |  | (B) |  | (A) + (B) |  |
| " | (A) + (B) |  | (A) + (B) |  |  |
| " | (A) + (B) | (A) + (B) | (A) + (B) |  |  |
| " |  | (A) + (B) | (A) + (B) |  |  |
| " |  | (A) + (B) | (A) + (B) | (A) + (B) |  |
| " |  | (A) + (B) | (A) + (B) | (A) + (B) | (A) + (B) |
| " |  |  | (A) + (B) | (A) + (B) |  |
| " |  |  | (A) + (B) | (A) + (B) | (A) + (B) |
| " |  |  |  | (A) + (B) | (A) + (B) |

2 to 8 weeks after application, the herbicidal efficacy of the active compounds or active compound mixtures is scored visually in comparison to untreated control plots. Damage to and development of all above-ground parts of the plants are recorded. Scoring is carried out according to a percent scale (100% effect=all plants have died; 50% effect=50% of the plants and the green parts of the plants have died; 0% effect=no noticable effect=like control plot. The means of the scores of in each case 2-4 plots are calculated.

The comparison showed that most of the combinations according to the invention have a higher, in some cases a considerably higher, activity than the sum of the activities of the individual herbicides. In substantial sections of the scoring period, the activities were higher than the expected values according to Colby (cf. scoring in Example 1), which indicates synergism. In contrast, the cereal plants were damaged only to an insignificant extent, if at all, by the treatment with the herbicidal compositions.

General abbreviations used in the tables:
g of AS/ha=gram of active substance (100% active compound) per hectare
$E^A$=sum of the herbicidal effects of the individual applications
(=expected value according to the addition method)

$E^C$=expected value according to Colby (cf. scoring for Table 1)
"cereal LL"=®Liberty-Link cereal which is tolerant or resistant to glufosinate-ammonium 4. Herbicidal Effect and Compatibility with Crop Plants (Greenhouse Trial)

4.1 Materials and Methods Used

The trials were carried out under greenhouse conditions (test pots, diameter 8 cm, spray application using 300 l of water/hectare, 2 repetitions, 6 to 8 plants per pot).

Application was by post-emergence treatment of the harmful plants and the wheat plants, as indicated in the tables. At the time of application, the harmful plants were at the 2-4-leaf growth stage. The application rates of the herbicidally active compounds used on their own or in combinations are listed in the results tables.

Scoring was by visual comparison of the treated with the untreated controls (0-100% scale, 14 days after the application. The results (means for all plants per pot and means of two repetitions per pot and treatment) are listed in Tables 4 to 8 below.

4.2 Abbreviations used in Tables 4 to 6
application rate g/ai=application rate in grams of active compound per hectare
ai=active ingredient (of an active compound content of 100%)
GA=glufosinate-ammonium
wheat tolerant
to GA=GA-tolerant wheat (GMO)
$E^C$=expected value according to Colby, ($E^C$=A+B−A×B/100)=
=for ternary combinations: (A+B)+C−(A+B)×C/100
$E^A$=expected value according to the addition method ($E^A$=A+B)
Δ=difference (%) between observed value —%— vs. expected value (%) (observed value minus expected value)
examination: observed values for (A), (B) and (A)+(B) in %
scoring: observed value (%) greater>than $E^C/E^A$:->synergism (+Δ)
observed value (%) equal to =$E^C/E^A$->additive effect (+−0Δ)
observed value (%) smaller<than $E^A/E^C$->antagonism (−Δ)

4.3 Results of the Greenhouse Trials with Combinations of Glufosinate-Ammonium (GA) A1.1 and B1.1 and Further Partners (C) on Wheat (GA-Tolerant) and Harmful Plants

TABLE 4

Crop plant compatibility in wheat (GA-tolerant) and herbicidal efficacy with respect to *Matricaria chamomilla*

| Active ingredient (ai) | Application rate g of ai/ha | Damage to crop plants (%) wheat (GA-tolerant) | Herbicidal efficacy (%) *Matricaria chamomilla* |
|---|---|---|---|
| (A1.1) GA | 100 | 10 | 50 |
| (B1.1) | 5 | 0 | 20 |
| (A1.1) + (B1.1) | 100 + 5 | 10 | 30 ($E^C$ = 60; Δ − 30) |
| (C5) amidosulfuron | 1.25 | 0 | 45 |
| (A1.1 + B1.1) + C5 | (100 + 5) + 1.25 | 10 | 85 ($E^C$ = 61; Δ + 24) |
| (C24) fenoxaprop-p-et. | 12.5 | 0 | 0 |
| (A1.1 + B1.1) + C24 | (100 + 5) + 12.5 | 0 | 50 ($E^C$ = 30; Δ + 20) |
| (C9) carfentrazone | 7.5 | 10 | 0 |
| (A1.1 + B1.1) + C9 | (100 + 5) + 7.5 | 5 | 90 ($E^C$ = 30; Δ + 60) |

TABLE 4-continued

Crop plant compatibility in wheat (GA-tolerant) and herbicidal efficacy with respect to *Matricaria chamomilla*

| Active ingredient (ai) | Application rate g of ai/ha | Damage to crop plants (%) wheat (GA-tolerant) | Herbicidal efficacy (%) *Matricaria chamomilla* |
|---|---|---|---|
| (C32) flurtamone | 62.5 | 15 | 25 |
| (A1.1 + B1.1) + C32 | (100 + 5) + 62.5 | 15 | 80 ($E^C = 48; \Delta + 32$) |
| (C37) imazamox | 5 | 15 | 0 |
| (A1.1 + B1.1) + C37 | (100 + 5) + 5 | 15 | 85 ($E^C = 30; \Delta + 55$) |
| (C58) pinoxaden | 5 | 0 | 0 |
| (A1.1 + B1.1) + C58 | (100 + 5) + 5 | 5 | 70 ($E^C = 30; \Delta + 40$) |
| (C60) propoxycarbazone-Na | 10 | 10 | 10 |
| (A1.1 + B1.1) + C60 | (100 + 5) + 10 | 10 | 80 ($E^C = 37; \Delta + 43$) |
| (C61) pyrasulfutole | 25 | 0 | 50 |
| (A1.1 + B1.1) + C61 | (100 + 5) + 25 | 0 | 95 ($E^C = 65; \Delta + 30$) |
| (C66) thiencarbazone-me | 0.375 | 5 | 10 |
| (A1.1 + B1.1) + C66 | (100 + 5) + 0.375 | 10 | 80 ($E^C = 37; \Delta + 43$) |
| (C71) tribenuron | 0.5 | 0 | 0 |
| (A1.1 + B1.1) + C71 | (100 + 5) + 0.5 | 10 | 80 ($E^C = 30; \Delta + 50$) |
| (C74) metsulfuron | 0.375 | 0 | 30 |
| (A1.1 + B1.1) + C74 | (100 + 5) + 0.375 | 10 | 90 ($E^C = 30; \Delta + 60$) |
| (C42) isoproturon | 125 | 0 | 15 |
| (A1.1 + B1.1) + C42 | (100 + 5) + 125 | 0 | 90 ($E^C = 40; \Delta + 50$) |

TABLE 5

Crop plant compatibility in wheat (GA-tolerant) and herbicidal efficacy with respect to *Viola arvensis*

| Active ingredient (ai) | Application rate g of ai/ha | Damage to crop plants (%) wheat (GA-tolerant) | Herbicidal efficacy (%) *Viola arvensis* |
|---|---|---|---|
| (A1.1) GA | 100 | 10 | 50 |
| (B1.1) | 5 | 0 | 50 |
| (A1.1) + (B1.1) | 100 + 5 | 10 | 30 ($E^c = 75; \Delta - 45$) |
| (C7) bromoxynil | 100 | 0 | 20 |
| (A1.1 + B1.1) + C7 | (100 + 5) + 100 | 0 | 50 ($E^c = 44; \Delta + 6$) |
| (C25) florasulam | 1.25 | 0 | 20 |
| (A1.1 + B1.1) + C25 | (100 + 5) + 1.25 | 10 | 60 ($E^c = 44; \Delta + 16$) |
| (C52) mesosulfuron-me | 2.5 | 0 | 0 |
| (A1.1 + B1.1) + C52 | (100 + 5) + 2.5 | 15 | 60 ($E^c = 30; \Delta + 30$) |
| (C43) MCPA | 100 | 0 | 10 |
| (A1.1 + B1.1) + C43 | (100 + 5) + 100 | 0 | 50 ($E^c = 37; \Delta + 13$) |
| (C57) penoxulam | 5 | 0 | 5 |
| (A1.1 + B1.1) + C57 | (100 + 5) + 5 | 0 | 50 ($E^c = 33; \Delta + 17$) |

TABLE 6

Crop plant compatibility in wheat (GA-tolerant) and herbicidal efficacy with respect to *Brassica napus* (volunteer weed)

| Active ingredient (ai) | Application rate g of ai/ha | Damage to crop plants (%) wheat (GA-tolerant) | Herbicidal efficacy (%) *Brassica napus* |
|---|---|---|---|
| (A1.1) GA | 100 | 10 | 15 |
| (B1.1) | 5 | 0 | 60 |
| (A1.1) + (B1.1) | (100 + 5) | 0 | 30 ($E^c = 66; \Delta - 36$) |
| (C12) clodinafop | 12.5 | 0 | 0 |
| (A1.1 + B1.1) + C12 | (100 + 5) + 12.5 | 10 | 65 ($E^c = 30; \Delta + 35$) |
| (C18) diflufenican | 50 | 10 | 30 |
| (A1.1 + B1.1) + C18 | (100 + 5) + 50 | 10 | 70 ($E^c = 51; \Delta + 19$) |

TABLE 7

Crop plant compatibility in wheat (GA-tolerant) and herbicidal efficacy with respect to *Setaria viridis*

| Active ingredient (ai) | Application rate g of ai/ha | Damage to crop plants (%) wheat (GA-tolerant) | Herbicidal efficacy (%) *Setaria viridis* |
|---|---|---|---|
| (A1.1) GA | 100 | 10 | 90 |
| (A1.1) + (B1.1) | 5 | 0 | 20 |

TABLE 7-continued

Crop plant compatibility in wheat (GA-tolerant) and herbicidal efficacy with respect to *Setaria viridis*

| Active ingredient (ai) | Application rate g of ai/ha | Damage to crop plants (%) wheat (GA-tolerant) | Herbicidal efficacy (%) *Setaria viridis* |
|---|---|---|---|
| (A1.1) + B1.1 | (100 + 5) | 10 | <u>70</u> (E$^e$ = 92; Δ − 22) |
| (C28) flufenacet | 50 | 0 | 20 |
| (A1.1) + (B1.1) + C28 | (100 + 5) + 50 | 10 | 97 (E$^e$ = 76; Δ + 21) |
| (C40) iodosulfuron-me-Na | 1 | 0 | 10 |
| (A1.1 + B1.1) + C40 | (100 + 5) + 1 | 10 | 85 (E$^e$ = 72; Δ + 13) |
| (C43) MCPA | 100 | 0 | 0 |
| (A1.1 + B1.1) + C43 | (100 + 5) + 100 | 0 | 85 (E$^e$ = 70; Δ + 15) |
| (C13) 2,4-D | 50 | 0 | 0 |
| (A1.1 + B1.1) + C13 | (100 + 5) + 50 | 0 | 90 (E$^e$ = 70; Δ + 20) |

TABLE 8

Crop plant compatibility in wheat (GA-tolerant) and herbicidal efficacy with respect to *Lolium multiflorum*

| Active ingredient (ai) | Application rate g of ai/ha | Damage to crop plants (%) wheat (GA-tolerant) | Herbicidal efficacy (%) *Lolium multiflorum* |
|---|---|---|---|
| (A1.1) GA | 100 | 10 | 15 |
| (B1.1) | 5 | 0 | 0 |
| (A1.1) + (B1.1) | (100 + 5) | 10 | <u>15</u> (E$^e$ = 15; Δ +− 0) |
| (C62) pyroxulam | 1.25 | 10 | 40 |
| (A1.1 + B1.1) + C62 | (100 + 5) + 1.25 | 15 (E$^e$ = 19; Δ − 4) | 70 (E$^e$ = 49; Δ + 21) |
| (C4) mefenpyr-di-et | 60 | 0 | 0 |
| (A1.1 + B1.1 + C62 + C4 | (100 + 5) + 1.25 + C4 | 5 (E$^e$ = 15; Δ − 10) safening | 80 (E$^e$ = 15; Δ + 65) |

The invention claimed is:

1. A herbicide combination for controlling harmful plants in cereal crops, wherein the herbicide combination comprises synergistically effective amounts of (A) a herbicide selected from the group consisting of glufosinate-ammonium and L-glufosinate-ammonium, and (B) a herbicide of the formula (B1)

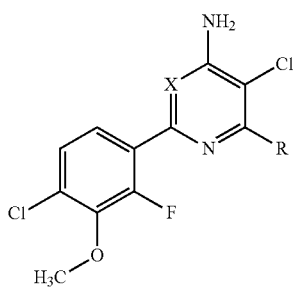

in which X represents CH and R represents CO$_2$H or a herbicidal active derivative thereof, at a weight ratio of component (A) to component (B) of from 750:1 to 1:60, with the proviso that components (A) and (B) are used in quantities and ratios such that their combined herbicidal efficacy is less than expected for combinations of the individual components (A) and (B), and (C) a herbicide selected from the group consisting of amidosulfuron (C5), bromoxynil (C7), carfentrazone-ethyl (C9), clodinafop-propargyl (C12), 2,4-D (C13), diflufenican (C18), fenoxaprop-P-ethyl (C24), florasulam (C25), flufenacet (thiafluamide) (C28), flurtamone (C32), imazamox (C37), iodosulfuron-methyl-sodium (C40), isoproturon (C42), MCPA (C43), mesosulfuron-methyl-sodium (C52), penoxsulam (C57), pinoxaden (C58), propoxycarbazone-sodium (C60), pyrasulfotole (C61), pyroxsulam (C62), thien-carbazone-methyl (C66), and tribenuron (C71), at a weight ratio of component (C) to component (B) of from 1:10 to 1.25:1, wherein the cereal crops are tolerant to the herbicides (A) and (B) present in the combination, wherein said combination of components (A) and (B) and (C) exhibits herbicidal efficacy greater than expected for combinations of the individual components (A), (B), and (C) and greater than expected for the herbicidal efficacy of component (C) and the collective herbicidal efficacy of a mixture of components (A) and (B).

2. A combination as claimed in claim 1 wherein the herbicide combination comprises, in addition to components (A), (B), and (C), at least one further active compound selected from the group consisting of safeners, plant growth regulators, fungicides and insecticides.

3. A combination as claimed in claim 1, wherein the cereal crop is tolerant to the herbicide combination in the presence of a safener.

4. A combination as claimed in claim 1, wherein the herbicide combination further comprises cyprosulfamide (C2).

5. A combination as claimed in claim 1, wherein the herbicide combination comprises, as component (A), glufosinate-ammonium.

6. A combination as claimed in claim 1, wherein the cereal crop comprises wheat.

7. A combination as claimed in claim 1, wherein the cereal crop is tolerant to herbicides which inhibit acetolactate synthase (ALS), EPSP synthase or hydroxyphenylpyruvate dioxygenase (HPPD).

8. A combination as claimed in claim 7, wherein the cereal crop is tolerant to at least one sulfonylurea herbicide, at least one sulfonamide herbicide, glyphosate, mesotrione, tembotrione, topramezone, bicyclopyrone or isoxaflutole.

9. A combination as claimed in claim 1, wherein component (B) is selected from the group consisting of
- 4-amino-3-chloro-6-(4-chloro-2-fluoro-3-methoxyphenyl)pyridine-2-carboxylic acid (B1.0),
- methyl 4-amino-3-chloro-6-(4-chloro-2-fluoro-3-methoxyphenyl)pyridine-2-carboxylate (B1.1),
- ethyl 4-amino-3-chloro-6-(4-chloro-2-fluoro-3-methoxyphenyl)pyridine-2-carboxylate (B1.2),
- n-propyl 4-amino-3-chloro-6-(4-chloro-2-fluoro-3-methoxyphenyl)pyridine-2-carboxylate (B1.3),
- isopropyl 4-amino-3-chloro-6-(4-chloro-2-fluoro-3-methoxyphenyl)pyridine-2-carboxylate (B1.4),
- n-butyl 4-amino-3-chloro-6-(4-chloro-2-fluoro-3-methoxyphenyl)pyridine-2-carboxylate (B1.5),
- 2-butyl 4-amino-3-chloro-6-(4-chloro-2-fluoro-3-methoxyphenyl)pyridine-2-carboxylate (B1.6),
- tert-butyl 4-amino-3-chloro-6-(4-chloro-2-fluoro-3-methoxyphenyl)pyridine-2-carboxylate (B1.7),
- allyl 4-amino-3-chloro-6-(4-chloro-2-fluoro-3-methoxyphenyl)pyridine-2-carboxylate (B1.8),
- 2-butoxyethyl 4-amino-3-chloro-6-(4-chloro-2-fluoro-3-methoxyphenyl)pyridine-2-carboxylate (B1.9),
- 4-amino-3-chloro-6-(4-chloro-2-fluoro-3-methoxyphenyl)pyridine-2-carboxylic acid triethylammonium salt (B1.10), and
- 4-amino-3-chloro-6-(4-chloro-2-fluoro-3-methoxyphenyl)pyridine-2-carboxylic acid potassium salt (B1.11).

10. A combination as claimed in claim 9, wherein the active compound (B) is selected from the group consisting of 4-amino-3-chloro-6-(4-chloro-2-fluoro-3-methoxyphenyl)pyridine-2-carboxylic acid (B1.0) and methyl 4-amino-3-chloro-6-(4-chloro-2-fluoro-3-methoxy-phenyl)pyridine-2-carboxylate (B1.1).

11. A herbicidal composition comprising synergistically effective amounts of
(A) glufosinate-ammonium;
(B) a compound selected from the group consisting of
- 4-amino-3-chloro-6-(4-chloro-2-fluoro-3-methoxyphenyl)pyridine-2-carboxylic acid (B1.0),
- methyl 4-amino-3-chloro-6-(4-chloro-2-fluoro-3-methoxyphenyl)pyridine-2-carboxylate (B1.1),
- ethyl 4-amino-3-chloro-6-(4-chloro-2-fluoro-3-methoxyphenyl)pyridine-2-carboxylate (B1.2),
- n-propyl 4-amino-3-chloro-6-(4-chloro-2-fluoro-3-methoxyphenyl)pyridine-2-carboxylate (B1.3),
- isopropyl 4-amino-3-chloro-6-(4-chloro-2-fluoro-3-methoxyphenyl)pyridine-2-carboxylate (B1.4),
- n-butyl 4-amino-3-chloro-6-(4-chloro-2-fluoro-3-methoxyphenyl)pyridine-2-carboxylate (B1.5),
- 2-butyl 4-amino-3-chloro-6-(4-chloro-2-fluoro-3-methoxyphenyl)pyridine-2-carboxylate (B1.6),
- tert-butyl 4-amino-3-chloro-6-(4-chloro-2-fluoro-3-methoxyphenyl)pyridine-2-carboxylate (B1.7),
- allyl 4-amino-3-chloro-6-(4-chloro-2-fluoro-3-methoxyphenyl)pyridine-2-carboxylate (B1.8),
- 2-butoxyethyl 4-amino-3-chloro-6-(4-chloro-2-fluoro-3-methoxyphenyl)pyridine-2-carboxylate (B1.9),
- 4-amino-3-chloro-6-(4-chloro-2-fluoro-3-methoxyphenyl)pyridine-2-carboxylic acid triethylammonium salt (B1.10), and
- 4-amino-3-chloro-6-(4-chloro-2-fluoro-3-methoxyphenyl)pyridine-2-carboxylic acid potassium salt (B1.11), at a weight ratio of component (A) to component (B) of from 750:1 to 1:60, with the proviso that components (A) and (B) are used in quantities and ratios such that their combined herbicidal efficacy is less than expected for combinations of the individual components (A) and (B); and (C) a herbicide selected from the group consisting of amidosulfuron (C5), bromoxynil (C7), carfentrazone-ethyl (C9), clodinafop-propargyl (C12), 2,4-D (C13), diflufenican (C18), fenoxaprop-P-ethyl (C24), florasulam (C25), flufenacet (thiafluamide) (C28), flurtamone (C32), imazamox (C37), iodosulfuron-methyl-sodium (C40), isoproturon (C42), MCPA (C43), mesosulfuron-methyl-sodium (C52), penoxsulam (C57), pinoxaden (C58), propoxycarbazone-sodium (C60), pyrasulfotole (C61), pyroxsulam (C62), thien-carbazone-methyl (C66), and tribenuron (C71), at a weight ratio of component (C) to component (B) of from 1:10 to 1.25:1, wherein said combination of components (A) and (B) and (C) exhibits herbicidal efficacy greater than expected for combinations of the individual components (A), (B), and (C) and greater than expected for the herbicidal efficacy of component (C) and the collective herbicidal efficacy of a mixture of components (A) and (B).

12. The herbicidal composition as claimed in claim 11 wherein the active compound (B) is selected from the group consisting of 4-amino-3-chloro-6-(4-chloro-2-fluoro-3-methoxyphenyl) pyridine-2-carboxylic acid (B1.0) and methyl 4-amino-3-chloro-6-(4-chloro-2-fluoro-3-methoxyphenyl) pyridine-2-carboxylate (B1.1).

13. The herbicidal composition as claimed in claim 11, further comprising a safener.

14. The herbicidal composition as claimed in claim 11, further comprising cloquintocet(-mexyl) (C1), cyprosulfamide (C2), isoxadifen(-ethyl) (C3) or mefenpyr(-diethyl) (C4).

15. The herbicidal composition as claimed in claim 11, further comprising cyprosulfamide (C2).

16. The herbicidal composition as claimed in claim 11 wherein the active compound (B) is methyl 4-amino-3-chloro-6-(4-chloro-2-fluoro-3-methoxyphenyl) -pyridine-2-carboxylate (B1.1).

* * * * *